(12) United States Patent
Spangenberg et al.

(10) Patent No.: US 7,880,054 B2
(45) Date of Patent: Feb. 1, 2011

(54) PLANT CAD1-LIKE GENES AND THEIR USE

(75) Inventors: German Spangenberg, Bundoora (AU); Michael Emmerling, Greensborough (AU); Eng Kok Ong, Vermont South (AU); Timothy Ivor Sawbridge, Collingwood (AU)

(73) Assignee: Agriculture Victoria Services Pty Ltd, Attwood, Victoria (AU)

( * ) Notice: Subject to any disclaimer, the term of this patent is extended or adjusted under 35 U.S.C. 154(b) by 478 days.

(21) Appl. No.: 11/568,504

(22) PCT Filed: May 6, 2005

(86) PCT No.: PCT/AU2005/000647

§ 371 (c)(1),
(2), (4) Date: Sep. 24, 2007

(87) PCT Pub. No.: WO2005/108577

PCT Pub. Date: Nov. 17, 2005

(65) Prior Publication Data

US 2008/0163393 A1 Jul. 3, 2008

(30) Foreign Application Priority Data

May 6, 2004 (AU) .............................. 2004902426

(51) Int. Cl.
- *C12N 15/82* (2006.01)
- *C12N 15/00* (2006.01)
- *C12N 15/11* (2006.01)
- *C12N 15/29* (2006.01)
- *A01H 5/00* (2006.01)
- *A01H 5/10* (2006.01)

(52) U.S. Cl. .................. 800/284; 800/278; 800/285; 800/295; 435/320.1; 435/410; 536/23.1; 536/23.2; 536/23.6; 536/24.3; 536/24.5

(58) Field of Classification Search .................. None
See application file for complete search history.

(56) References Cited

U.S. PATENT DOCUMENTS

| 2002/0078474 A1 * | 6/2002 | Chiang et al. ............... 800/278 |
| 2003/0180751 A1 * | 9/2003 | Demmer et al. ................ 435/6 |

FOREIGN PATENT DOCUMENTS

| WO | 01/95702 | 12/2001 |
| WO | 02/26994 | 4/2002 |
| WO | 03/040306 | 5/2003 |

OTHER PUBLICATIONS

GenBank Accession AAK97809.1 "Cinnamyl alcohol dehydrogenase 1b [*Festuca arundinaceae*]" Sep. 4, 2001.
GenBank Accession AAL34328.1 "Cinnamyl alcohol dehydrogenase 1b [*Medicago sativa*]" Nov. 21, 2001.
GenBank Accession AF472592.1 "Cinnamyl alcohol dehydrogenase 1b [*Lolium perenne*]" Mar. 31, 2002.

* cited by examiner

*Primary Examiner*—Medina A Ibrahim
*Assistant Examiner*—Brent Page
(74) *Attorney, Agent, or Firm*—Larson & Anderson, LLC

(57) ABSTRACT

The present invention relates to polynucleotides encoding cinnamyl alcohol dehydrogenase (1) like (CAD1L) polypeptides. CAD1L polypeptides are produced in a plant in the same organs and the same developmental stages and processes of CAD1 and are likely to be involved in the same developmental processes as CAD enzymes. CAD1L-like sequences are also disclosed. They can be used for modification of, for example, lignification, cellulose, degradation, plant cell walls or plant defense response.

16 Claims, 15 Drawing Sheets

```
  1    GAGCATGGAT GATTTTTAAG TCTGTTTACT TTAACATGTG TTCTGTTGTC
 51    CTTTTAAGGC AAGAGCCCTG TGACTGACAG CGAAATAATC TAGCGAACAG
101    TTTTTGTGGT GTGGG
```

Figure 3

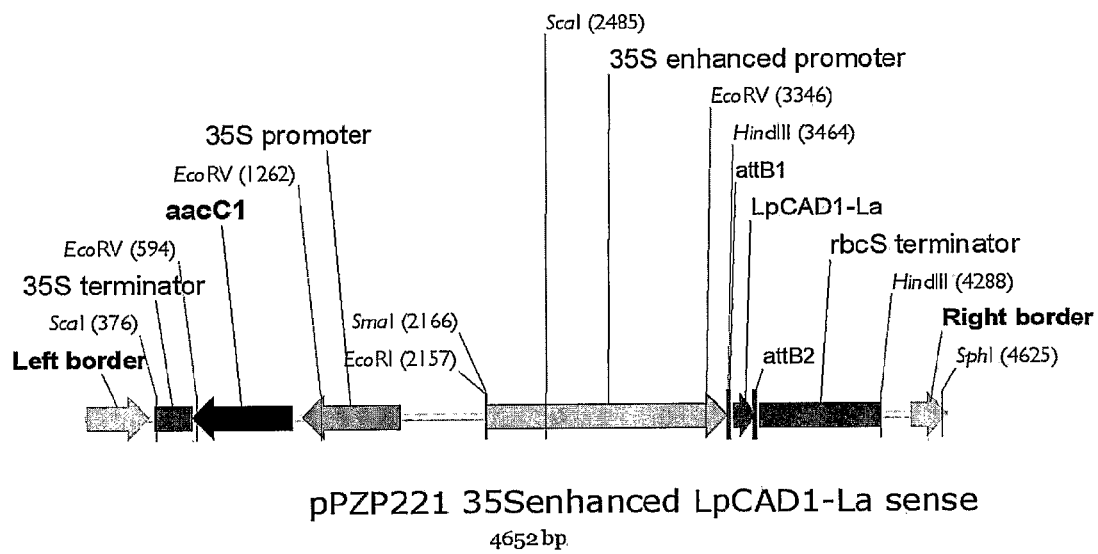
pPZP221 35Senhanced LpCAD1-La sense
4652 bp
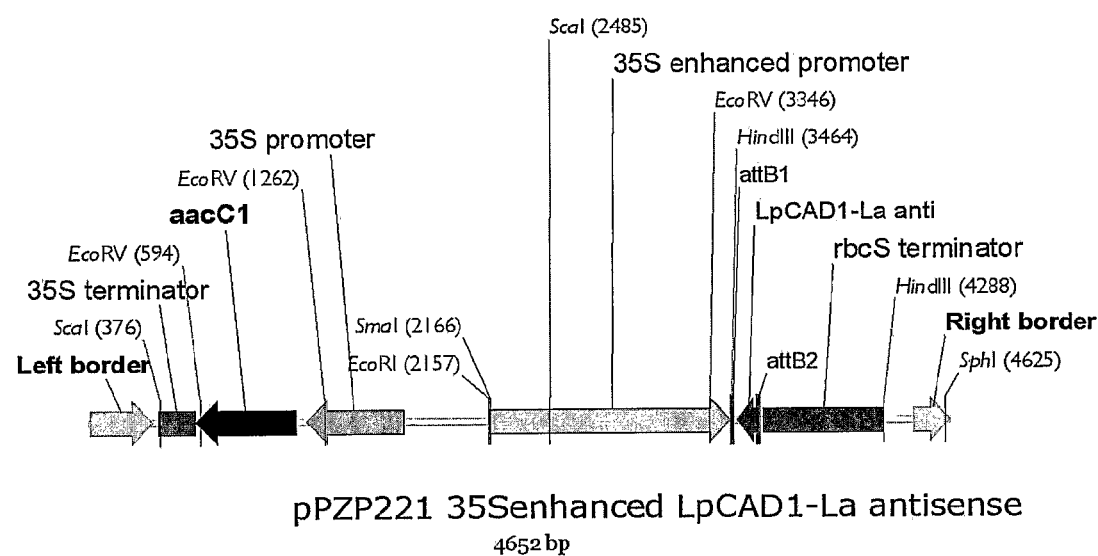
pPZP221 35Senhanced LpCAD1-La antisense
4652 bp
Figure 4

| | | | | | |
|---|---|---|---|---|---|
| 1 | ATTCAAGGCC | ATCTATTACA | GTAGCCAAAA | AAGGCAATAG | TACCACCCAT |
| 51 | CAAAACAAGA | AGGCATCCAA | TGAACTATTC | AGAGGGAGAT | TGGAAGGGAA |
| 101 | AGAAGAAATG | GTGAGGGGGG | TTGAGGATAC | AATAGATGAC | ACCTATTTGC |
| 151 | AATAATCTGC | TGGCTCAAAT | GTTGGCGGGA | GTGTGGATAT | TCTGATTGAT |
| 201 | GGATTTGTCC | CTCCGGCTAG | CAGTTGTTGC | TCCTATGTTT | ACTTTAGTGC |
| 251 | GGCTTCTACG | ATCATTTTTC | CCTCTCCTCC | AGCTACTGAA | CAGATTTTCT |
| 301 | TCTGGTCAGC | TCTCTGTTGC | ATACCAGTTA | GTAAATTACC | TGTTATTGAC |
| 351 | TTATCGTGCT | TAAAAAATTT | CAGTGGGCAA | TTTTGCTTGC | TTCTCTAAAA |
| 401 | GTAGCATATT | AAATGGTAGC | AAGGAGGATG | CTCTTCCAGC | TATAAATTTT |
| 451 | TTGCAGACAT | TTGTTGGTTT | GAACTGTCCA | AAGGTAAGCA | AACTAAATCA |
| 501 | GATTGTTGAG | CTATCATCAT | CTGCCTGCTC | AAATTATTTG | TGATAACGAA |
| 551 | TGTTTAATGT | TTTTGAACTA | TATGCAAAGC | TTCTATGTGT | TCTCTT |

Figure 5

```
  1    GGTGTCGGAG GATCTGATTT CCCCTCTCTT CTCCCTCTTG TGTTCGGTAA
 51    TACAAGCCGC AGGTATGGGC TGTCGATTCC GATCTCGCGC TCGTGGTGAT
101    TGGTCCGTTG AGATCTAGGT CTGGTGATTT CTGCTCTGTT CCGTCTCGTT
151    GGTATTGTAT ATTCTGCACT ACGCTGCTTC GATTCAGGGT CGCGGCTAGC
201    CTTTTTTTTT TCTGATTCCA CTTAGGTCGT GGCTAATCTG TTATTTGTCT
251    GACTGGTTTA GGGTCGTGGC TTACGTATTA TGTACTAATT GCTCACTTGA
301    TTCAGATCTG GCCAGAATAA TGATTCATAT AGATGTGTGC TCAGCTCGTT
351    GGCTTTGATT TCTGTTCGTT ATGCTTATGC TGGATTGCTC ATGTCAGTTT
401    AGTTGAATCC ATAGAGATAT TTGGCATTAT CGGAATGAGA AATCGAAGGT
451    TGTGGTTTGG ATCGGTCTGT TCCATTCAAG GTTGTCGATT CACTAATGTT
501    CTGCTAACAA ATGCTAGTTG CGATGAAAAA ACAACTATTC GTTATGCTGG
551    ATTACCCAGG TCGGTTTAGT TGATTCCATG GGCATGACTG GAATGAGAAA
601    TTAAAGGTTA TGGTTTGGAT TTGTCTGTTC CATTCAATGC TG
```

Figure 7

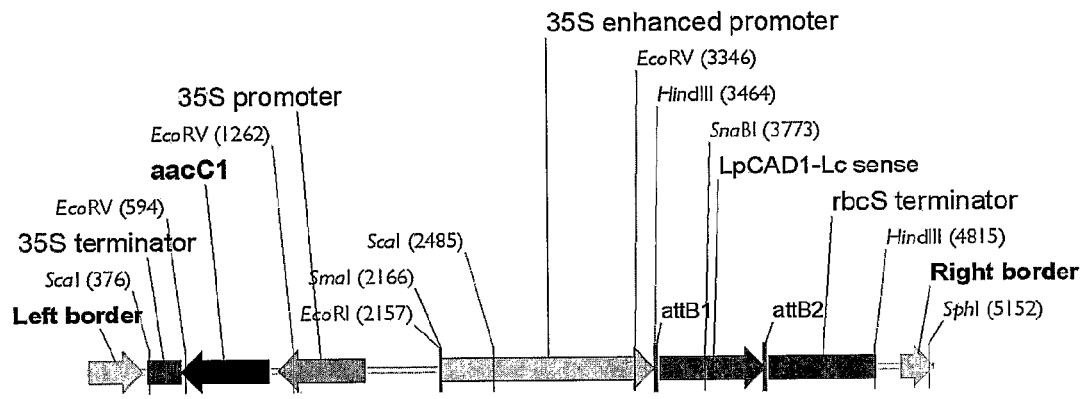
pPZP221 35Senhanced LpCAD1-Lc sense
5179 bp
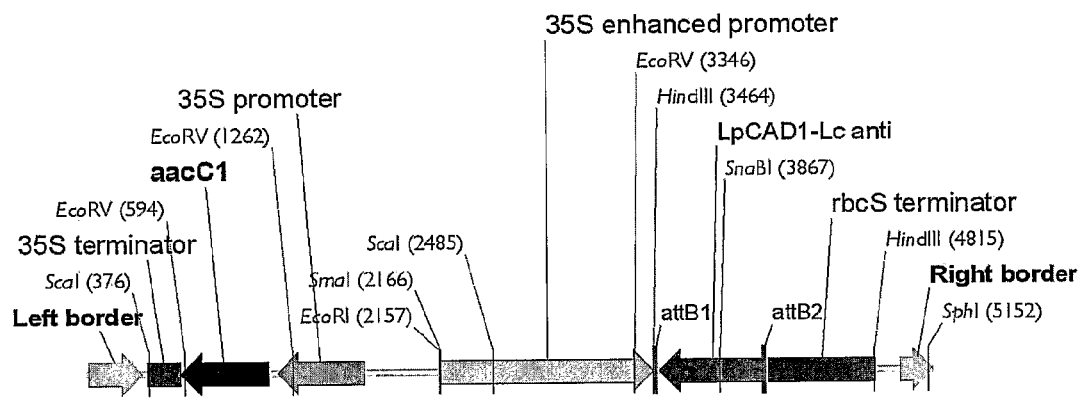
pPZP221 35Senhanced LpCAD1-Lc antisense
5179 bp
Figure 8

```
  1    TATCCTTGCT TCAGCTTTAG CTTCCAGCTG TGATTCGGTT TAACTAGCGT
 51    TTTCTCTGGT TTGATTTATT TGTGATGGCC CAATGGATTA TATGAAGAAC
101    TGAGATGAGT TCTTGTTGCT CTGGTTCTGA GCGTTGGCTT GAAAATAAAT
151    ATGTACCTAG GGCTGTGTTT GGACAACACG ACGTGTTTTT GTTTTATACC
201    CTGCCTCGTG CATGTCCTTG GTTGACAGCT CTTACATGCA CATGGTGACT
251    GTGCCTGTTA GTCTGCATGG CTGCTGGATG TGACTCAGTG CATCCTCCCT
301    TGTGGATCAG ATCGGCTGAG AAAGATCTTC CTTTTCCATT TCTTATTATT
351    ATTATTTGTT AACTTGGCCA CTTGGCTTTT CTTTACTTTT TTGTTCTCGG
401    TGTTTGTTTT GCAGGTGATA AGTTAAACAA GATGATCTGG GAACGTGGAC
451    GAAGGTTATG AGCTTCAAGA TTTAGTTTTA GGGGTTTATT TCCTTTTCTT
501    G
```

Figure 9

| | |
|---|---|
| 1 | GAGCATTCAT CTGGTAGAAA CCGCTCGGTT CAACTCAATG CTAAAAGAAT |
| 51 | GCTCGCGTCG CCATTTCTGC CACCAGTTGC GCTCTGGCCG GCCGGGCTCG |
| 101 | AAATCTGCTC GGCAATTTGC TCATCTATGT CTGATTGGAT TGGATTGTGC |
| 151 | TCCTCGGTGA AGCCCCTTCG AATTGATTGT ATTATCCGTT CTCCCTTCTC |
| 201 | TGATTGGTAT CTAAACAGAC CAGTGAGCCG CCCCTTCTAT TCTCCATCTT |
| 251 | CTGCATGCCA CCTCTCTCCA CTGTCTGTAT GCCGTCTCCA TTCGTGAGGT |
| 301 | AATTTTGATT AGTCGGACTC CTCCATTTGA AATATAATTT ACTGAATGGT |
| 351 | CTTCCAGCCC CATGTTCATC GCCTGATTCA CGTTTATTGG CTACTGGTGC |
| 401 | CGCGCGTCCT AGACATGACG GATCTGGTGT TGCCGTCGTG ACCTGCCTCA |
| 451 | CATTCCTCTG CTGTATAAGG TTAGCCTAGA ACTCAACATT CTCTCAATCC |
| 501 | CAATCCTCCT ATGTTGTCTT TCTGGGTAAC CACCGCAATT ATATGGCTGC |
| 551 | CCTGTTATTA TTTTTCCATG TCTCTTGAGT ATTTTCATAT ACCTTTGCAC |
| 601 | TTTCTTCTGA TTGAAACTCG AAGTTAGCTA TGCAAAAAAG ATCATTATAT |
| 651 | GCTCGGTGAG TTGCAGGATT ATTTGTTTTC AGCAACCAAG CTTTGCACCA |
| 701 | GCAACAAAAC TACTT |

Figure 11

```
  1    GAGCATTTAA CTTATTTATC AGTTAACTTG TTCAAGAAGA GTAGAGGACA
 51    ACAATCGTTG AAGTCTGAAC GAAGTGCTCA ACACACACAT ACTTAAAATT
101    TAGGTCAATG TGCTCATTAT TAACTTGATA TTAGCAAACT CTTCAACAAA
151    GTGATGCTTC CAACAATCAA CTAGATAAAC TTGCACAACG ATGAACCGAG
201    ATATTGATGT TGTTCTTGAG AGACAAGAAT AGGTTTAATC CATGCAAGCC
251    AAAAAAAAG AAGGATCAAG CTATATTTTA TCACAACTTC AATGCACCCG
301    AGCAAAAACA AGCCATCCAT GGAAACAGAA CTTTTAGGAC TAAATGAGGT
351    CATCCATATA TCATTTAACA GTTACAGTTT CCAACACCAG ATAAGATGCA
401    CACAAACTAG CAGAAGTCGA ACTAAACAAT CCACGAAGTA AATTCAAACC
451    CTCACAAGTG AAGGCCAGAT GAAGAAACTA AATGAGGTCA TGTGTATATG
501    TCATCTAACA GTTAGACAAT AATCTTAAGT ACC
```

Figure 13

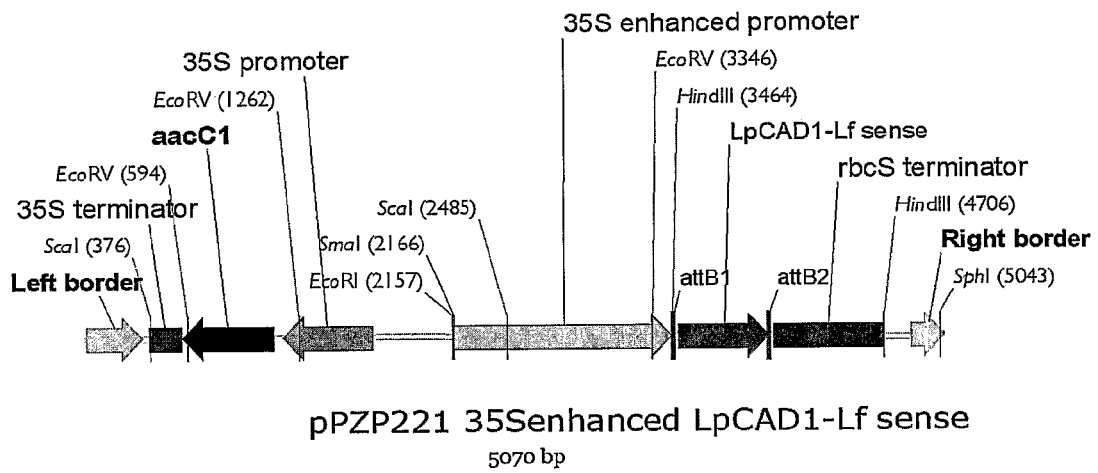
pPZP221 35Senhanced LpCAD1-Lf sense
5070 bp
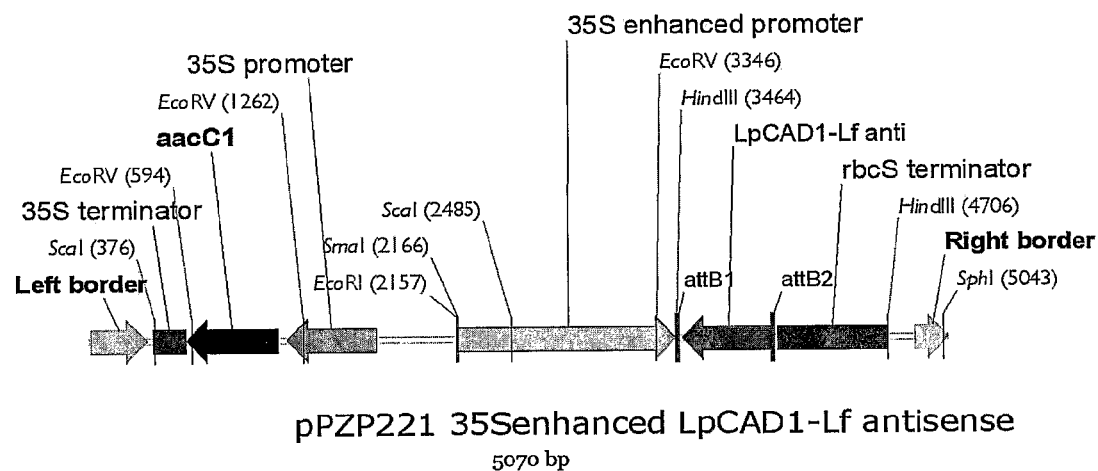
pPZP221 35Senhanced LpCAD1-Lf antisense
5070 bp
Figure 14

SEQUENCE LISTING

<160> NUMBER OF SEQ ID NOS: 6

<210> SEQ ID NO 1
<211> LENGTH: 115
<212> TYPE: DNA
<213> ORGANISM: Lolium perenne

<400> SEQUENCE: 1

```
gagcatggat gattttaag tctgtttact ttaacatgtg ttctgttgtc cttttaaggc    60
aagagccctg tgactgacag cgaaataatc tagcgaacag ttttgtggt gtggg         115
```

<210> SEQ ID NO 2
<211> LENGTH: 596
<212> TYPE: DNA
<213> ORGANISM: Lolium perenne

<400> SEQUENCE: 2

```
attcaaggcc atctattaca gtagccaaaa aaggcaatag taccacccat caaaacaaga    60
aggcatccaa tgaactattc agagggagat tggaagggaa agaagaaatg gtgaggggg    120 ttgaggatac aatagatgac acctatttgc aataatctgc tggctcaaat gttggcggga   180
gtgtggatat tctgattgat ggatttgtcc ctccggctag cagttgttgc tcctatgttt   240
actttagtgc ggcttctacg atcattttc cctctcctcc agctactgaa cagattttct    300
tctggtcagc tctctgttgc ataccagtta gtaaattacc tgttattgac ttatcgtgct   360 taaaaattt cagtgggcaa ttttgcttgc ttctctaaaa gtagcatatt aaatggtagc    420
aaggaggatg ctcttccagc tataaatttt ttgcagacat ttgttggttt gaactgtcca   480
aaggtaagca aactaaatca gattgttgag ctatcatcat ctgcctgctc aaattatttg   540
tgataacgaa tgtttaatgt ttttgaacta tatgcaaagc ttctatgtgt tctctt       596
```

<210> SEQ ID NO 3
<211> LENGTH: 642
<212> TYPE: DNA
<213> ORGANISM: Lolium perenne

<400> SEQUENCE: 3

```
ggtgtcggag gatctgattt cccctctctt ctccctcttg tgttcggtaa tacaagccgc    60
aggtatgggc tgtcgattcc gatctcgcgc tcgtggtgat tggtccgttg agatctaggt   120
ctggtgattt ctgctctgtt ccgtctcgtt ggtattgtat attctgcact acgctgcttc   180
gattcagggt cgcggctagc cttttttttt tctgattcca cttaggtcgt ggctaatctg   240
ttatttgtct gactggttta gggtcgtggc ttacgtatta tgtactaatt gctcacttga   300
ttcagatctg gccagaataa tgattcatat agatgtgtgc tcagctcgtt ggctttgatt   360
tctgttcgtt atgcttatgc tggattgctc atgtcagttt agttgaatcc atagagatat   420
ttggcattat cggaatgaga aatcgaaggt tgtggtttgg atcggtctgt tccattcaag   480
gttgtcgatt cactaatgtt ctgctaacaa atgctagttg cgatgaaaaa acaactattc   540
gttatgctgg attacccagg tcggtttagt tgattccatg gcatgactg gaatgagaaa    600 ttaaaggtta tggtttggat ttgtctgttc cattcaatgc tg                      642
```

<210> SEQ ID NO 4
<211> LENGTH: 501
<212> TYPE: DNA
<213> ORGANISM: Lolium perenne

<400> SEQUENCE: 4

```
tatccttgct tcagctttag cttccagctg tgattcggtt taactagcgt tttctctggt      60
ttgatttatt tgtgatggcc caatggatta tatgaagaac tgagatgagt tcttgttgct     120
ctggttctga gcgttggctt gaaaataaat atgtacctag ggctgtgttt ggacaacacg     180
acgtgttttt gttttatacc ctgcctcgtg catgtccttg gttgacagct cttacatgca     240
catggtgact gtgcctgtta gtctgcatgg ctgctggatg tgactcagtg catcctccct     300
tgtggatcag atcggctgag aaagatcttc cttttccatt tcttattatt attatttgtt     360
aacttggcca cttggctttt ctttactttt ttgttctcgg tgtttgtttt gcaggtgata     420
agttaaacaa gatgatctgg gaacgtggac gaaggttatg agcttcaaga tttagtttta     480
ggggtttatt tccttttctt g                                               501
```

<210> SEQ ID NO 5
<211> LENGTH: 715
<212> TYPE: DNA
<213> ORGANISM: Lolium perenne

<400> SEQUENCE: 5

```
gagcattcat ctggtagaaa ccgctcggtt caactcaatg ctaaaagaat gctcgcgtcg      60
ccatttctgc caccagttgc gctctggccg gccgggctcg aaatctgctc ggcaatttgc     120
tcatctatgt ctgattggat tggattgtgc tcctcggtga agccccttcg aattgattgt     180
attatccgtt ctcccttctc tgattggtat ctaaacagac cagtgagccg cccctttctat     240
tctccatctt ctgcatgcca cctctctcca ctgtctgtat gccgtctcca ttcgtgaggt     300
aattttgatt agtcggactc ctccatttga aatataattt actgaatggt cttccagccc     360
catgttcatc gcctgattca cgtttattgg ctactggtgc cgcgcgtcct agacatgacg     420
gatctggtgt tgccgtcgtg acctgcctca cattcctctg ctgtataagg ttagcctaga     480
actcaacatt ctctcaatcc caatcctcct atgttgtctt tctgggtaac caccgcaatt     540
atatggctgc cctgttatta tttttccatg tctcttgagt attttcatat accttttgcac    600
tttcttctga ttgaaactcg aagttagcta tgcaaaaaag atcattatat gctcggtgag     660
ttgcaggatt atttgttttc agcaaccaag cttttgcacca gcaacaaaac tactt           715
```

<210> SEQ ID NO 6
<211> LENGTH: 533
<212> TYPE: DNA
<213> ORGANISM: Lolium perenne

<400> SEQUENCE: 6

```
gagcatttaa cttatttatc agttaacttg ttcaagaaga gtagaggaca acaatcgttg      60
aagtctgaac gaagtgctca acacacacat acttaaaatt taggtcaatg tgctcattat     120
taacttgata ttagcaaact cttcaacaaa gtgatgcttc caacaatcaa ctagataaac     180
ttgcacaacg atgaaccgag atattgatgt tgttcttgag agacaagaat aggtttaatc     240
catgcaagcc aaaaaaaaag aaggatcaag ctatatttta tcacaacttc aatgcacccg     300
agcaaaaaca agccatccat ggaaacagaa cttttaggac taaatgaggt catccatata     360
tcatttaaca gttacagttt ccaacaccag ataagatgca cacaaactag cagaagtcga     420
actaaacaat cccacgaagta aattcaaacc ctcacaagtg aaggccagat gaagaaacta     480
aatgaggtca tgtgtatatg tcatctaaca gttagacaat aatcttaagt acc            533
```

US 7,880,054 B2

1

PLANT CAD1-LIKE GENES AND THEIR USE

The present invention relates to nucleic acid fragments encoding amino acid sequences for lignification-related enzymes in plants, and the use thereof for the modification of plant cell walls and/or defence response in plants.

Lignins are complex phenolic polymers that strengthen plant cell walls against mechanical and chemical degradation. The process of lignification typically occurs during secondary thickening of the walls of cells. Three monolignol precursors, sinapyl, coniferyl and p-coumaryl alcohol combine by dehydrogenative polymerisation to produce respectively the syringyl (S), guaiacyl (G) and hydroxyl (H) subunits of the lignin polymer, which can also become linked to cell-wall polysaccharides through the action of peroxidases and other oxidative enzymes.

Biosynthesis of the monolignol precursors is a multistep process beginning with the aromatic amino-acids phenylalanine (and tyrosine in grasses). Lignin biosynthesis is initiated by the conversion of phenylalanine into cinnamate through the action of phenylalanine ammonia lyase (PAL). The second enzyme of the pathway is cinnamate-4-hydroxylase (C4H), responsible for the conversion of cinnamate to p-coumarate. The second hydroxylation step in the pathway is catalyzed by p-coumarate-3-hydroxylase (C3H) producing caffeic acid. Caffeic acid is then O-methylated by caffeic acid O-methyltransferase (OMT) to form ferulic acid. Ferulic acid is subsequently converted into 5-hydroxyferulate through the last hydroxylation reaction of the general phenylpropanoid pathway catalised by ferulate-5-hydroxylase (F5H). The 5-hydroxyferulate produced by F5H is then O-methylated by OMT, the same enzyme that carries out the O-methylation of caffeic acid. The cinnamic acids are converted by action of the 4-coumarate:CoA ligase (4CL) and caffeoyl-CoA 3-O-mehtyltransferase (CCoAMT) into the corresponding CoA derivatives. It is the final two reduction/dehydrogenation steps of the pathway, catalysed by cinnamoyl CoA reductase (CCR) and cinnamyl alcohol dehydrogenase (CAD) that are considered to be specific to lignin biosynthesis. The three monolignols, sinapyl, coniferyl and p-coumaryl alcohols, are then polymerised by extracellular peroxidases (PER) and laccases (LAC) to yield lignins. The proportions of monolignols incorporated into the lignin polymers vary depending on plant species, tissue, developmental stage and sub-cellular location.

Cinnamyl alcohol dehydrogenase (CAD) governs the last committed step of the lignin biosynthesis pathway, converting the hydroxycinnamaldehydes to their corresponding cinnamyl alcohols (monolignols). Different isoforms of CAD have been reported. CAD1 is monomeric and able to utilise a range of substituted and unsubstituted benzaldehydes. CAD2 is a homo- or heterodimer that has been found in all plants examined and the angiosperm enzyme uses all three cinnamaldehydes whereas the gymnosperm enzyme has a poor affinity for sinapaldehyde. Defence-responsive isoforms (CAD3) have also been reported.

Lignification of plant cell walls has effects on their structural, conductive or defensive roles.

Dry matter digestibility of forages has been negatively correlated with lignin content. In addition, natural mutants of lignin biosynthetic enzymes in maize, sorghum and pearl millet that have higher rumen digestibility have been characterised as having lower lignin content and altered S/G subunit ratio. Lignification of plant cell walls is the major factor identified as responsible for lowering digestibility of forage tissues as they mature.

2

Lignification also affects efficiency of cellulose extraction in the pulping process of wood for paper production. Cell wall digestibility, pulping efficiency and feed (grazed, cut hay, silage) quality can thus be increased by the manipulation of enzymes involved in the biosynthesis of lignins.

Perennial ryegrass (*Lolium perenne* L.) is a key pasture grass in temperate climates throughout the world. Perennial ryegrass is also an important turf grass.

It would be desirable to have methods of altering lignification in plants. For example it may be desirable to reduce the activity of key lignin biosynthetic related enzymes in order to reduce lignin content and/or alter lignin composition for enhancing dry matter digestibility and improving herbage quality. For other applications it may be desirable to enhance lignin biosynthesis to increase lignin content and/or alter lignin composition, for example to increase mechanical strength of wood, to increase mechanical strength, to reduce plant height, to reduce lodging and to improve disease resistance.

While nucleic acid sequences encoding some of the enzymes involved in lignification have been isolated for certain species of plants, there remains a need for materials useful in the modification of lignification in a wide range of plants, and for methods for their use.

It is an object of the present invention to overcome, or at least alleviate, one or more of these needs in light of the prior art.

In one aspect, the present invention provides substantially isolated nucleic acids encoding amino acid sequences (ie polypeptides) of cinnamyl alcohol dehydrogenase 1 like enzymes (CAD1L). These sequences are termed CAD1-like on the basis of the similarity of their expression pattern to CAD. The present invention further provides substantially isolated nucleic acids or nucleic acid fragments complementary and antisense to these CAD1L-encoding nucleic acids.

The present invention also provides substantially isolated nucleic acid fragments encoding amino acid sequences for a class of proteins, which are related to CAD1L. Such proteins are referred to herein as CAD1L-like. The genes which encode these proteins are expressed in a similar manner for CAD1L. This CAD1L-like class of polypeptides includes functionally active fragments or variants of CAD1L polypeptides and non-CAD1L polypeptides having similar functional activity to CAD1L polypeptides. Also provided are substantially isolated nucleic acids or nucleic acid fragments complementary and antisense to these CAD1L-like-encoding nucleic acid fragments.

In another aspect, the present invention provides a substantially purified or isolated nucleic acid or nucleic acid fragment encoding a cinnamyl alcohol dehydrogenase 1 like polypeptide (CAD1L) or complementary or antisense to a sequence encoding CAD1L and including a nucleotide sequence selected from the group consisting of (a) sequences shown in FIGS. 3, 5, 7, 9, 11 and 13 hereto (SEQ ID NOS 1, 2, 3, 4, 5 and 6 respectively); (b) complements of the sequences recited in (a); and (c) sequences antisense to the sequences recited in (a) or (b).

In another aspect, the present invention provides a substantially purified or isolated RNA or RNA fragment encoding a cinnamyl alcohol dehydrogenase 1 like polypeptide (CAD1L) or complementary or antisense to such a sequence (or a functionally active fragment or variant thereof) encoding CAD1L and including, or alternatively consisting essentially of, a nucleotide sequence selected from the group consisting of (a) sequences shown in FIGS. 3, 5, 7, 9, 11 and 13 hereto (SEQ ID NOS 1, 2, 3, 4, 5 and 6 respectively); (b)

complements of the sequences recited in (a); and (c) sequences antisense to the sequences recited in (a) or (b).

In one embodiment, the substantially purified or isolated nucleic acid or nucleic acid fragment encoding a cinnamyl alcohol dehydrogenase 1 like polypeptide (CAD1L) or complementary or antisense to a sequence encoding CAD1L consists essentially of a nucleotide sequence selected from the group consisting of (a) sequences shown in FIGS. 3, 5, 7, 9, 11 and 13 hereto (SEQ ID NOS 1, 2, 3, 4, 5 and 6 respectively); (b) complements of the sequences recited in (a); and (c) sequences antisense to the sequences recited in (a) or (b). In another embodiment, the substantially purified or isolated nucleic acid or nucleic acid fragment consists essentially of a functionally active fragment or variant of such a sequence.

The invention also provides a substantially purified or isolated nucleic acid or nucleic acid fragment encoding a CAD1L-like polypeptide, or complementary or antisense to a sequence encoding CAD1L-like polypeptide, the CAD1L-like polypeptide having similar functional activity to a CAD1L polypeptide encoded by a nucleic acid sequence including a nucleotide sequence selected from the group consisting of (a) sequences shown in FIGS. 3, 5, 7, 9, 11 and 13 hereto (SEQ ID NOS 1, 2, 3, 4, 5 and 6 respectively); (b) complements of the sequences recited in (a); and (c) sequences antisense to the sequences recited in (a) or (b). Furthermore, the present invention also provides a substantially purified or isolated nucleic acid or nucleic acid fragment including a functionally active fragment or variant of such a sequence.

The invention also provides a substantially purified or isolated RNA or RNA fragment encoding a CAD1L-like polypeptide, or complementary or antisense to a sequence encoding CAD1L-like polypeptide, and including, or alternatively consisting essentially of, a nucleotide sequence corresponding to a sequence selected from the group consisting of (a) sequences shown in FIGS. 3, 5, 7, 9, 11 and 13 hereto (SEQ ID NOS 1, 2, 3, 4, 5 and 6 respectively); (b) complements of the sequences recited in (a); (c) sequences antisense to the sequences recited in (a) or (b); and (d) functionally active fragments or variants of such sequences.

The nucleic acids or nucleic acid fragments may be obtained from ryegrass (*Lolium*) or fescue (*Festuca*) species. These species may be of any suitable type, including Italian or annual ryegrass, perennial ryegrass, tall fescue, meadow fescue and red fescue. Preferably the species is a ryegrass, more preferably perennial ryegrass (*L. perenne*).

Nucleic acids according to the invention may be full-length genes or part thereof, and are also referred to as "nucleic acid fragments" and "nucleotide sequences" in this specification. For convenience, the expression "nucleic acid or nucleic acid fragment" is used to cover all of these.

The nucleic acid or nucleic acid fragment may be of any suitable type and includes DNA (such as cDNA or genomic DNA) and RNA (such as mRNA) that is single- or double-stranded, optionally containing synthetic, non-natural or altered nucleotide bases, and combinations thereof.

The term "isolated" means that the material is removed from its original environment (eg. the natural environment if it is naturally occurring). For example, a naturally occurring nucleic acid fragment or polypeptide present in a living plant is not isolated, but the same nucleic acid fragment or polypeptide separated from some or all of the coexisting materials in the natural system, is isolated. Such an isolated nucleic acid fragment could be part of a vector and/or such nucleic acid fragments could be part of a composition, and still be isolated in that such a vector or composition is not part of its natural environment.

By "functionally active" in respect of a nucleotide sequence is meant that the fragment or variant (such as an analogue, derivative or mutant) is capable of modifying lignin biosynthesis and/or cellulose degradation in a plant. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence, more preferably at least approximately 90% identity, most preferably at least approximately 95% identity. Such functionally active variants and fragments include, for example, those having nucleic acid changes which result in conservative amino acid substitutions of one or more residues in the corresponding amino sequence. Preferably the fragment has a size of at least 30 nucleotides, more preferably at least 45 nucleotide, most preferably at least 60 nucleotides.

By "functionally active" in the context of a polypeptide is meant that the fragment or variant has one or more of the biological properties for the enzymes CAD1L and CAD1L-like. Additions, deletions, substitutions and derivatizations of one or more of the amino acids are contemplated so long as the modifications do not result in loss of functional activity of the fragment or variant. Preferably the functionally active fragment or variant has at least approximately 60% identity to the relevant part of the above mentioned sequence, more preferably at least approximately 80% identity, most preferably at least approximately 90% identity. Such functionally active variants and fragments include, for example, those having conservative amino acid substitutions of one or more residues in the corresponding amino acid sequence. Preferably the fragment has a size of at least 10 amino acids, more preferably at least 15 amino acids, most preferably at least 20 amino acids.

By "operatively linked" is meant that said regulatory element is capable of causing expression of said nucleic acid in a plant cell and said terminator is capable of terminating expression of said nucleic acid in a plant cell. Preferably, said regulatory element is upstream of said nucleic acid and said terminator is downstream of said nucleic acid.

By "an effective amount" is meant an amount sufficient to result in an identifiable phenotypic trait in said plant, or a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor, the entire disclosure of which is incorporated herein by reference.

It will also be understood that the term "comprises" (or its grammatical variants) as used in this specification is equivalent to the term "includes" and should not be taken as excluding the presence of other elements or features.

In a preferred embodiment of this aspect of the invention, the substantially purified or isolated nucleic acid fragment encoding a CAD1L or CAD1L-like protein includes a nucleotide sequence selected from the group consisting of sequences shown in FIGS. 3, 5, 7, 9, 11 and 13 hereto (SEQ ID NOS: 1, 2, 3, 4, 5 and 6, respectively);

The nucleic acid fragments of the present invention may be used to isolate cDNAs and genes encoding homologous proteins from the same or other plant species. Additionally, genes encoding other CAD1L or CAD1L-like enzymes, either as cDNAs or genomic DNAs, may be isolatable directly by using all or a portion of the nucleic acid fragments of the present invention as hybridisation probes to screen libraries from the desired plant employing the methodology known to those skilled in the art. Specific oligonucleotide probes based upon the nucleic acid sequences of the present invention can be designed and synthesized by methods known in the art. Moreover, the entire sequences can be used directly to synthesize DNA probes by methods known to the skilled artisan such as random primer DNA labelling, nick translation, or end-labelling techniques, or RNA probes using available in vitro transcription systems. In addition, specific primers can be designed and used to amplify a part or all of the sequences of the present invention. The resulting amplification products can be labelled directly during amplification reactions or labelled after amplification reactions, and used as probes to isolate full length cDNA or genomic fragments under conditions of appropriate stringency.

In addition, two short segments of the nucleic acid fragments of the present invention may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the nucleic acid fragments of the present invention, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, those skilled in the art can follow the RACE protocol (Frohman et al. (1988) *Proc. Natl. Acad Sci.* USA 85:8998, the entire disclosure of which is incorporated herein by reference) to generate cDNAs by using PCR to amplify copies of the region between a single point in the transcript and the 3' or 5' end. Using commercially available 3' RACE and 5' RACE systems (BRL), specific 3' or 5' cDNA fragments can be isolated (Ohara et al. (1989) *Proc. Natl. Acad Sci* USA 86:5673; Loh et al. (1989) *Science* 243:217). Products generated by the 3' and 5' RACE procedures can be combined to generate full-length cDNAs.

In a second aspect of the present invention there is provided a substantially purified or isolated polypeptide selected from the group consisting of CAD1L and CAD1L-like enzymes.

Preferably the polypeptide is from a ryegrass (*Lolium*) or fescue (*Festuca*) species. The ryegrass (*Lolium*) or fescue (*Festuca*) species may be of any suitable type, including Italian or annual ryegrass, perennial ryegrass, tall fescue, meadow fescue and red fescue. Preferably the species is a ryegrass, more preferably perennial ryegrass (*L. perenne*).

In a preferred embodiment of this aspect of the invention, there is provided a substantially purified or isolated CAD1L and CAD1L-like polypeptide including an amino acid sequence selected from the group of sequences translated from nucleotide sequences shown in FIGS. 3, 5, 7, 9, 11 and 13 hereto (SEQ ID NOS: 1, 2, 3, 4, 5 and 6 respectively); and functionally active fragments and variants thereof.

In a further embodiment of this aspect of the invention, there is provided a polypeptide recombinantly produced from a nucleic acid according to the present invention. Techniques for recombinantly producing polypeptides are well known to those skilled in the art.

Availability of the nucleotide sequences of the present invention and deduced amino acid sequences facilitates immunological screening of cDNA expression libraries. Synthetic peptides representing portions of the instant amino acid sequences may be synthesized. These peptides can be used to immunise animals to produce polyclonal or monoclonal antibodies with specificity for peptides and/or proteins comprising the amino acid sequences. These antibodies can be then used to screen cDNA expression libraries to isolate full-length cDNA clones of interest.

A genotype is the genetic constitution of an individual or group. Variations in genotype are essential in commercial breeding programs, in determining parentage, in diagnostics and fingerprinting, and the like. Genotypes can be readily described in terms of genetic markers. A genetic marker identifies a specific region or locus in the genome. The more genetic markers, the finer defined is the genotype. A genetic marker becomes particularly useful when it is allelic between organisms because it then may serve to unambiguously identify an individual. Furthermore, a genetic marker becomes particularly useful when it is based on nucleic acid sequence information that can unambiguously establish a genotype of an individual and when the function encoded by such nucleic acid is known and is associated with a specific trait. Such nucleic acids and/or nucleotide sequence information including single nucleotide polymorphisms (SNPs), variations in single nucleotides between allelic forms of such nucleotide sequence, can be used as perfect markers or candidate genes for the given trait.

In a further aspect of the present invention there is provided a method of isolating a nucleic acid of the present invention including a single nucleotide polymorphism (SNP), said method including sequencing nucleic acid fragments from a nucleic acid library.

The nucleic acid library may be of any suitable type and is preferably a cDNA library. The nucleic acid fragments may be isolated from recombinant plasmids or may be amplified, for example using polymerase chain reaction. The sequencing may be performed by techniques known to those skilled in the art.

In a further aspect of the present invention, there is provided use of nucleic acids of the present invention including SNP's, and/or nucleotide sequence information thereof, as molecular genetic markers.

In a further aspect of the present invention there is provided use of a nucleic acid according to the present invention, and/or nucleotide sequence information thereof, as a molecular genetic marker. More particularly, nucleic acids according to the present invention and/or nucleotide sequence information thereof may be used as a molecular genetic marker for quantitative trait loci (QTL) tagging, QTL mapping, DNA fingerprinting and in marker assisted selection, particularly in ryegrasses and fescues. Even more particularly, nucleic acids according to the present invention and/or nucleotide sequence information thereof may be used as molecular genetic markers in forage and turf grass improvement, e.g. tagging QTLs for herbage quality traits, dry matter digestibility, mechanical stress tolerance, disease resistance, insect pest resistance, plant stature, leaf and stem colour. Even more particularly, sequence information revealing SNPs in allelic variants of the nucleic acids of the present invention and/or nucleotide sequence information thereof may be used as molecular genetic markers for QTL tagging and mapping and in marker assisted selection, particularly in ryegrasses and fescues.

In a still further aspect of the present invention there is provided a construct including a nucleic acid according to the present invention. The construct may be a vector. In a preferred embodiment of this aspect of the invention, the vector may include a regulatory element such as a promoter, a nucleic acid according to the present invention and a terminator; said regulatory element, nucleic acid and terminator being operatively linked.

The vector may be of any suitable type and may be viral or non-viral. The vector may be an expression vector. Such vectors include chromosomal, non-chromosomal and synthetic nucleic acid sequences, eg. derivatives of plant viruses; bacterial plasmids; derivatives of the Ti plasmid from *Agrobacterium tumefaciens*, derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable, or integrative or viable in the plant cell.

The regulatory element and terminator may be of any suitable type and may be endogenous to the target plant cell or may be exogenous, provided that they are functional in the target plant cell.

In another embodiment, the vector may include more than one nucleic acid. The nucleic acids within the same vector may have identical or differing sequences. In one preferred embodiment, the vector has at least two nucleic acids encoding functionally similar enzymes. For example, as disclosed in this specification, the nucleic acids may be selected from the group consisting of LpCAD1La, LpCAD1Lb, LpCAD1Lc, LpCAD1Ld, LpCAD1Le and LpCAD1Lf. Moreover, a second nucleotide sequence may encode another cinnamyl alcohol dehydrogenase or another lignification-related enzyme.

Preferably the regulatory element is a promoter. A variety of promoters which may be employed in the vectors of the present invention are well known to those skilled in the art. Factors influencing the choice of promoter include the desired tissue specificity of the vector, and whether constitutive or inducible expression is desired and the nature of the plant cell to be transformed (eg. monocotyledon or dicotyledon). Particularly suitable constitutive promoters include the Cauliflower Mosaic Virus 35S (CaMV 35S) promoter, the maize Ubiquitin promoter, and the rice Actin promoter.

A variety of terminators which may be employed in the vectors of the present invention are also well known to those skilled in the art. It may be from the same gene as the promoter sequence or a different gene. Particularly suitable terminators are polyadenylation signals, such as the CaMV 35S polyA and other terminators from the nopaline synthase (nos) and the octopine synthase (ocs) genes.

The vector, in addition to the regulatory element, the nucleic acid of the present invention and the terminator, may include further elements necessary for expression of the nucleic acid, in different combinations, for example vector backbone, origin of replication (ori), multiple cloning sites, spacer sequences, enhancers, introns (such as the maize Ubiquitin Ubi intron), antibiotic resistance genes and other selectable marker genes (such as the neomycin phosphotransferase (npt2) gene, the hygromycin phosphotransferase (hph) gene, the phosphinothricin acetyltransferase (bar or pat) gene), and reporter genes (such as beta-glucuronidase (GUS) gene (gusA)). The vector may also contain a ribosome binding site for translation initiation. The vector may also include appropriate sequences for amplifying expression.

As an alternative to use of a selectable marker gene to provide a phenotypic trait for selection of transformed host cells, the presence of the vector in transformed cells may be determined by other techniques well known in the art, such as PCR (polymerase chain reaction), Southern blot hybridisation analysis, histochemical GUS assays, northern and Western blot hybridisation analyses.

Those skilled in the art will appreciate that the various components of the vector are operatively linked, so as to result in expression of said nucleic acid. Techniques for operatively linking the components of the vector of the present invention are well known to those skilled in the art. Such techniques include the use of linkers, such as synthetic linkers, for example including one or more restriction enzyme sites.

The vectors of the present invention may be incorporated into a variety of plants, including monocotyledons (such as grasses from the genera *Lolium, Festuca, Paspalum, Pennisetum, Panicum* and other forage and turfgrasses, corn, rice, sugarcane, oat, wheat and barley), dicotyledons (such as arabidopsis, tobacco, soybean, canola, cotton, potato, chickpea, medics, white clover, red clover, subterranean clover, alfalfa, eucalyptus, poplar, hybrid aspen) and gymnosperms (pine tree). In a preferred embodiment, the vectors are used to transform monocotyledons, preferably grass species such as ryegrasses (*Lolium* species) and fescues (*Festuca* species), even more preferably a ryegrass, most preferably perennial ryegrass, including forage- and turf-type cultivars.

Techniques for incorporating the vectors of the present invention into plant cells (for example by transduction, transfection or transformation) are well known to those skilled in the art. Such techniques include *Agrobacterium* mediated introduction, electroporation to tissues, cells and protoplasts, protoplast fusion, injection into reproductive organs, injection into immature embryos and high velocity projectile introduction to cells, tissues, calli, immature and mature embryos. The choice of technique will depend largely on the type of plant to be transformed.

Cells incorporating the vectors of the present invention may be selected, as described above, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

In a further aspect of the present invention there is provided a plant cell, plant, plant seed or other plant part, including, e.g. transformed with, a vector of the present invention.

The plant cell, plant, plant seed or other plant part may be from any suitable species, including monocotyledons, dicotyledons and gymnosperms. In a preferred embodiment the plant cell, plant, plant seed or other plant part is from a monocotyledon, preferably a grass species, more preferably a ryegrass (*Lolium* species) or fescue (*Festuca* species), even more preferably a ryegrass, most preferably perennial ryegrass, including both forage- and turf-type cultivars.

The present invention also provides a plant, plant seed or other plant part derived from a plant cell of the present invention. The present invention also provides a plant, plant seed or other plant part derived from a plant of the present invention.

In a further aspect of the present invention there is provided a method of modifying lignification and defence response in a plant, said method including introducing into said plant an effective amount of a nucleic acid and/or a vector according to the present invention or a plant seed or other plant part derived from a plant of the present invention.

Using the methods and materials of the present invention, plant lignification and defence may be increased or decreased. They may be increased, for example, by incorporating additional copies of a sense nucleic acid of the present invention. They may be decreased, for example, by incorporating an antisense nucleic acid or dsRNA or small interfering RNA (siRNA) derived from the nucleotide sequences of the present invention. In addition, the number of copies of genes encoding for different enzymes involved in lignification and defence may be manipulated to modify the composition of lignin and plant cell walls.

In a still further aspect of the present invention there is provided a lignin or modified lignin or a cellulose or modified cellulose substantially or partially purified or isolated from a plant, plant seed or other plant part of the present invention. Such lignins may be modified from naturally occurring lignins in terms of their monomeric composition or ratios of individual monolignols, the presence of novel monolignols, the degree of linkage and/or nature of linkages between lignins and other plant cell wall components. Such cellulose may be modified from naturally occurring cellulose in terms of the degree of polymerisation (number of units), and/or degree of branching and/or nature of linkages between units and/or nature of linkages between cellulose and other plant cell wall components.

In a further aspect of the present invention there is provided a preparation for transforming a plant comprising at least one nucleic acid according to the present invention. The preparation may contain vectors or other constructs to facilitate administration to and/or transformation of the plant with the nucleic acid.

The present invention will now be more fully described with reference to the accompanying Examples and drawings. It should be understood, however, that the description following is illustrative only and should not be taken in any way as a restriction on the generality of the invention described above.

In the Figures:

FIG. 3 shows the nucleotide sequence of the cDNA fragment LpCAD1-La (Seq ID No. 1).

FIG. 4 shows plasmid maps of sense and antisense constructs of LpCAD1-La in pPZP221:35S$^2$ binary transformation vector.

FIG. 5 shows the nucleotide sequence of the cDNA fragment LpCAD1-Lb (Seq ID No. 2).

FIG. 7 shows the nucleotide sequence of the cDNA fragment LpCAD1-Lc (Seq ID No. 3).

FIG. 8 shows plasmid maps of sense and antisense constructs of LpCAD1-Lc in pPZP221:35S$^2$ binary transformation vector.

FIG. 9 shows the nucleotide sequence of the cDNA fragment LpCAD1-Ld (Seq ID No. 4).

FIG. 11 shows the nucleotide sequence of the cDNA fragment LpCAD1-Le (Seq ID No. 5).

FIG. 13 shows the nucleotide sequence of the cDNA fragment LPCAD1-Lf (Seq ID No. 6).

FIG. 14 shows plasmid maps of sense and antisense constructs of LpCAD1-Lf in pPZP221:35S$^2$ binary transformation vector.

EXAMPLE 1

Figure 1:
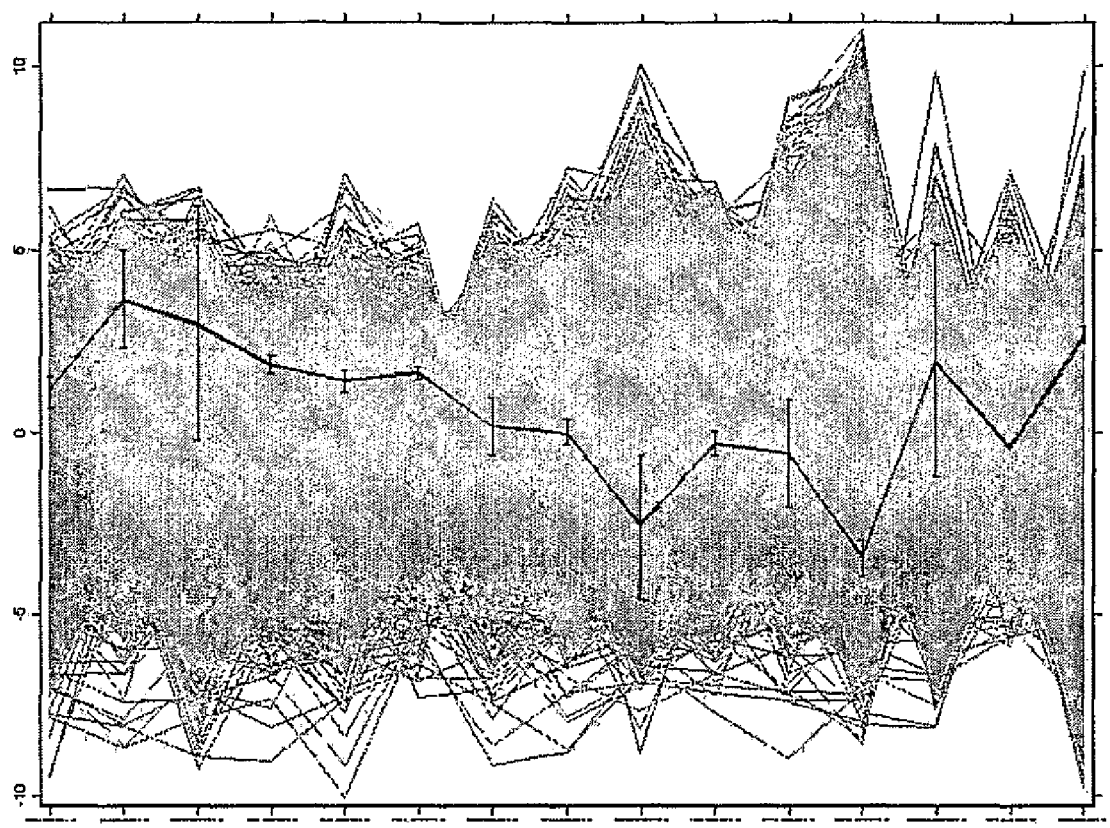
FIG. 1 shows the microarray based expression profile of LpCAD1 in perennial ryegrass as log ratio of its expression values.
Figure 2:
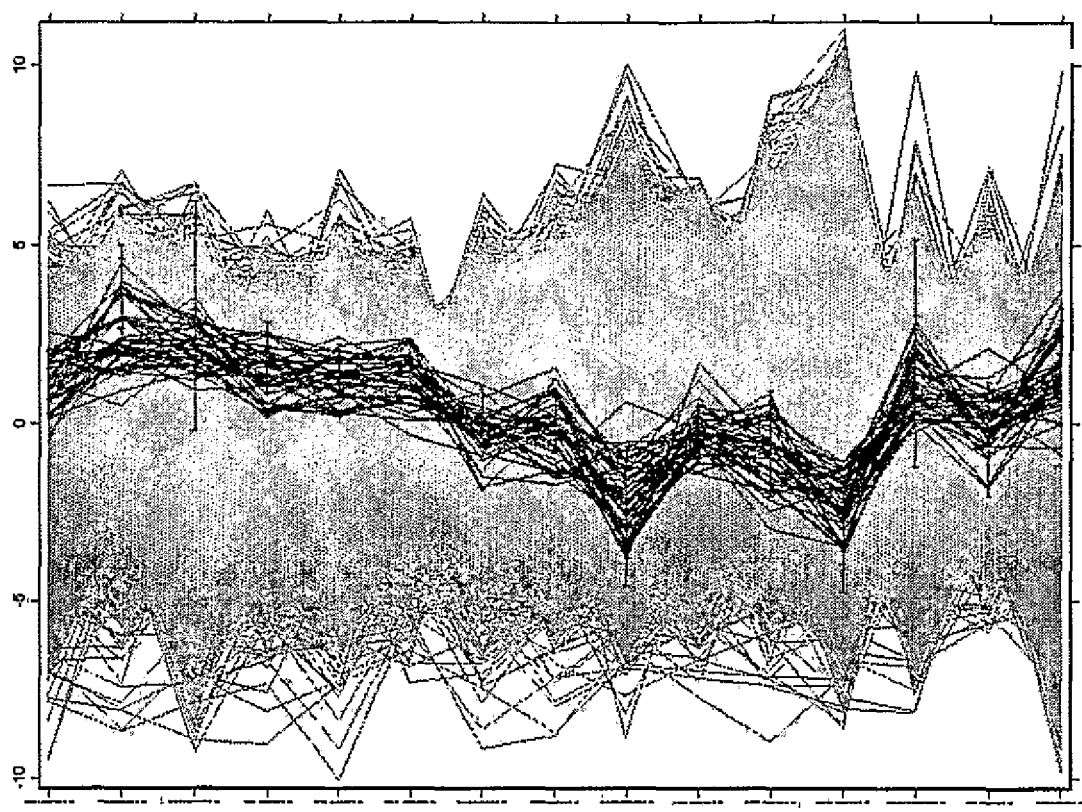
FIG. 2 shows the expression profiling of LpCAD1L genes using LpCAD1 as template gene in perennial ryegrass as log ratios of genes matching LpCAD1 at an Euclidian distance of 4.4393.
Figure 6:
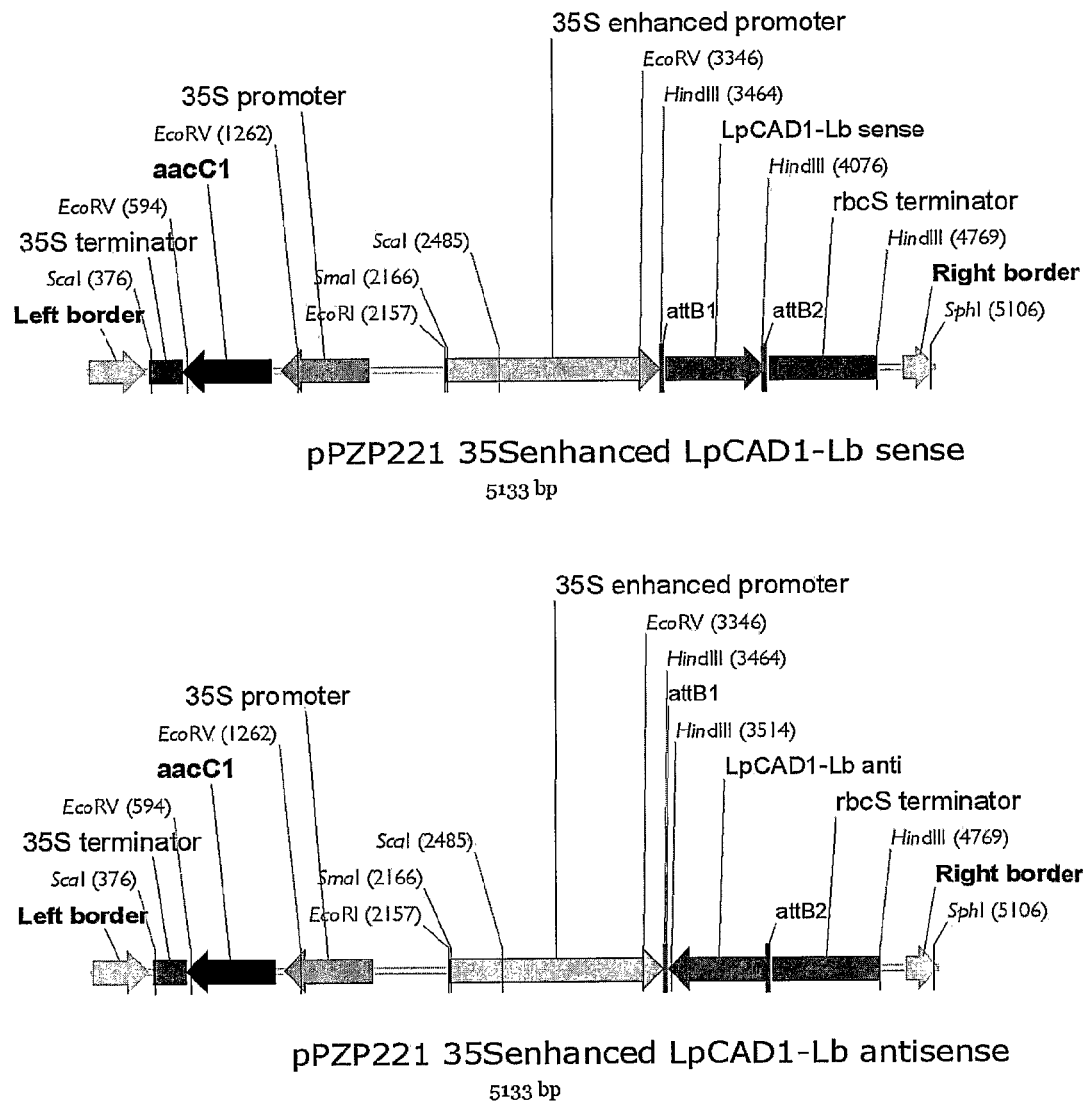
FIG. 6 shows plasmid maps of sense and antisense constructs of LpCAD1-Lb in pPZP221:35S$^2$ binary transformation vector.
Figure 10:
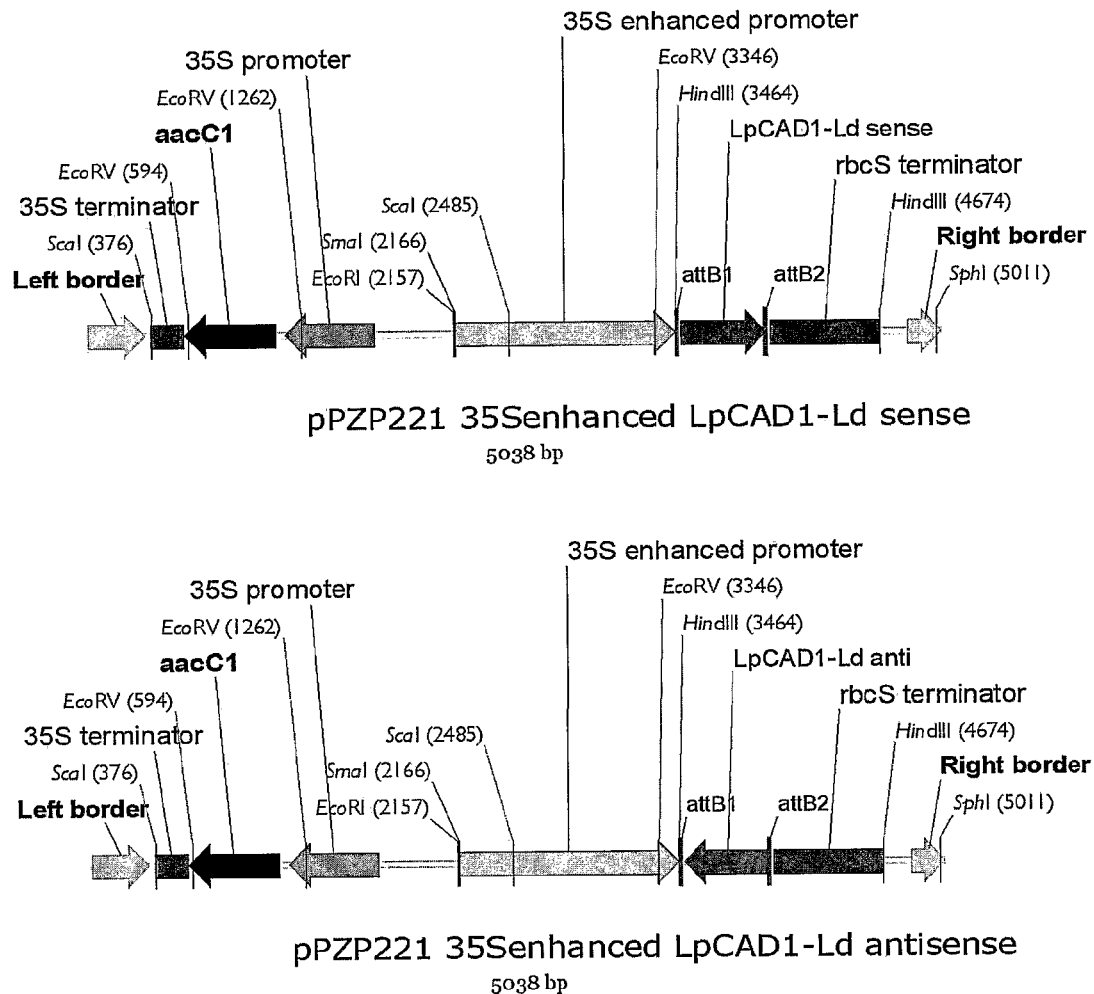
FIG. 10 shows plasmid maps of sense and antisense constructs of LpCAD1-Ld in pPZP221:35S$^2$ binary transformation vector.
Figure 12:
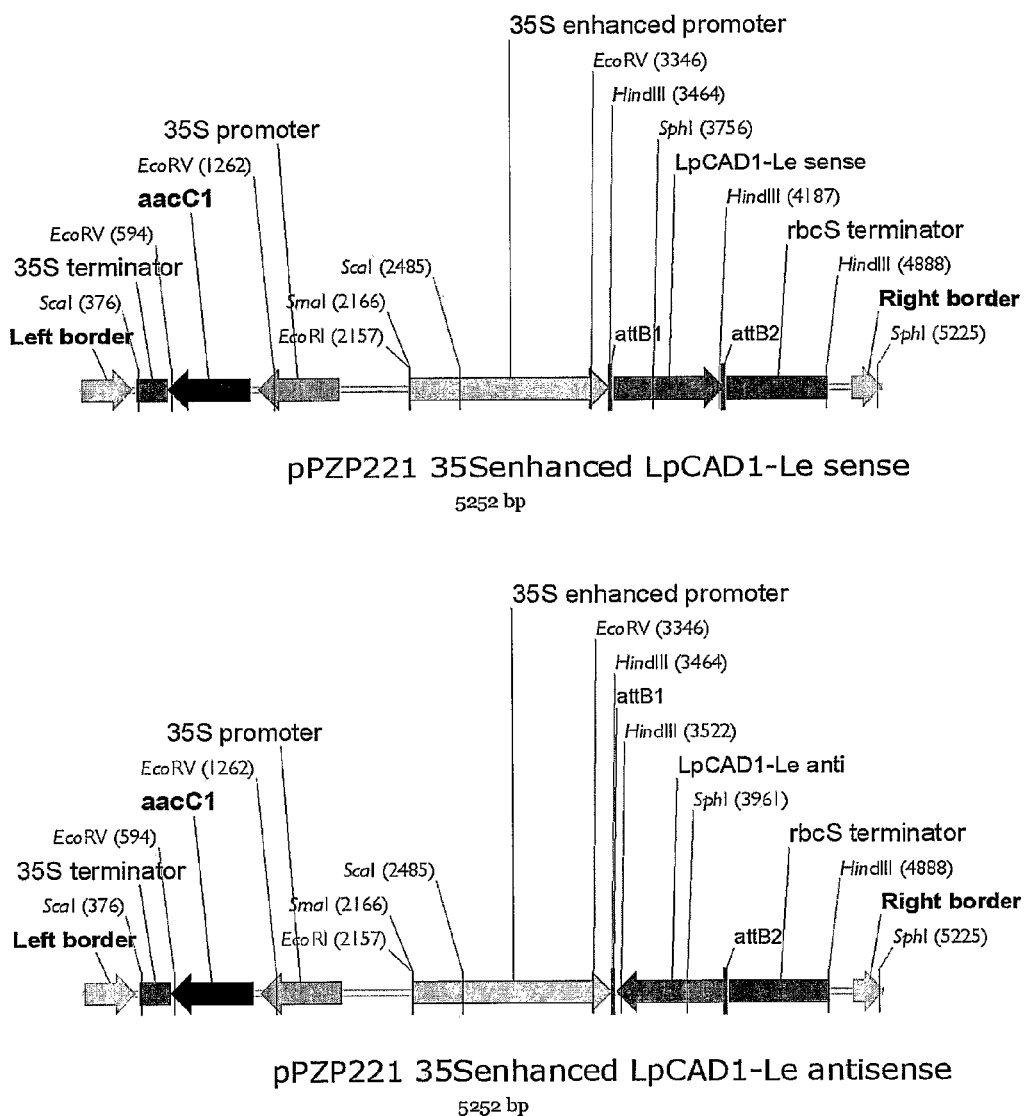
FIG. 12 shows plasmid maps of sense and antisense constructs of LpCAD1-Le in pPZP221:35S$^2$ binary transformation vector.

Preparation of cDNA Libraries, Isolation and Sequencing of cDNAs for Identification of cDNAs Coding for CAD1L from Perennial Ryegrass (*Lolium perenne*)

cDNA libraries representing mRNAs from various organs and tissues of perennial ryegrass (*Lolium perenne*) were prepared. The characteristics of the libraries are described below (Table 1).

TABLE 1 cDNA libraries from perennial ryegrass (*Lolium perenne*)

| Library | Organ/Tissue |
|---|---|
| 01rg | Roots from 3-4 day old light-grown seedlings |
| 02rg | Leaves from 3-4 day old light-grown seedlings |
| 03rg | Etiolated 3-4 day old dark-grown seedlings |
| 04rg | Whole etiolated seedlings (1-5 day old and 17 days old) |
| 05rg | Senescing leaves from mature plants |
| 06rg | Whole etiolated seedlings (1-5 day old and 17 days old) |
| 07rg | Roots from mature plants grown in hydroponic culture |
| 08rg | Senescent leaf tissue |
| 09rg | Whole tillers and sliced leaves (0, 1, 3, 6, 12 and 24 h after harvesting) |
| 10rg | Embryogenic suspension-cultured cells |
| 11rg | Non-embryogenic suspension-cultured cells |
| 12rg | Whole tillers and sliced leaves (0, 1, 3, 6, 12 and 24 h after harvesting) |
| 13rg | Shoot apices including vegetative apical meristems |
| 14rg | Immature inflorescences including different stages of inflorescence meristem and inflorescence development |
| 15rg | Defatted pollen |
| 16rg | Leaf blades and leaf sheaths (rbcL, rbcS, cab, wir2A subtracted) |
| 17rg | Senescing leaves and tillers |
| 18rg | Drought-stressed tillers (pseudostems from plants subjected to PEG-simulated drought stress) |

TABLE 1-continued cDNA libraries from perennial ryegrass (*Lolium perenne*)

| Library | Organ/Tissue |
|---|---|
| 19rg | Non-embryogenic suspension-cultured cells subjected to osmotic stress (grown in media with half-strength salts) (1, 2, 3, 4, 5, 6, 24 and 48 h after transfer) |
| 20rg | Non-embryogenic suspension-cultured cells subjected to osmotic stress (grown in media with double-strength salts) (1, 2, 3, 4, 5, 6, 24 and 48 h after transfer) |
| 21rg | Drought-stressed tillers (pseudostems from plants subjected to PEG-simulated drought stress) |
| 22rg | Spikelets with open and maturing florets |
| 23rg | Mature roots (specific subtraction with leaf tissue) |

The cDNA libraries may be prepared by any of many methods available. For example, total RNA may be isolated using the Trizol method (Gibco-BRL, USA) or the RNeasy Plant Mini kit (Qiagen, Germany), following the manufacturers' instructions. cDNAs may be generated using the SMART PCR cDNA synthesis kit (Clontech, USA), cDNAs may be amplified by long distance polymerase chain reaction using the Advantage 2 PCR Enzyme system (Clontech, USA), cDNAs may be cleaned using the GeneClean spin column (Bio 101, USA), tailed and size fractionated, according to the protocol provided by Clontech. The cDNAs may be introduced into the pGEM-T Easy Vector system 1 (Promega, USA) according to the protocol provided by Promega. The cDNAs in the pGEM-T Easy plasmid vector are transfected into *Escherichia coli* Epicurian coli XL10-Gold ultra competent cells (Stratagene, USA) according to the protocol provided by Stratagene.

Alternatively, the cDNAs may be introduced into plasmid vectors for first preparing the cDNA libraries in Uni-ZAP XR vectors according to the manufacturer's protocol (Stratagene Cloning Systems, La Jolla, Calif., USA). The Uni-ZAP XR libraries are converted into plasmid libraries according to the protocol provided by Stratagene. Upon conversion, cDNA inserts will be contained in the plasmid vector pBluescript. In addition, the cDNAs may be introduced directly into precut pBluescript II SK(+) vectors (Stratagene) using T4 DNA ligase (New England Biolabs), followed by transfection into *E. coli* DH10B cells according to the manufacturer's protocol (GIBCO BRL Products).

Once the cDNA inserts are in plasmid vectors, plasmid DNAs are prepared from randomly picked bacterial colonies containing recombinant plasmids, or the insert cDNA sequences are amplified via polymerase chain reaction using primers specific for vector sequences flanking the inserted cDNA sequences. Plasmid DNA preparation may be performed robotically using the Qiagen QiaPrep Turbo kit (Qiagen, Germany) according to the protocol provided by Qiagen. Amplified insert DNAs are sequenced in dye-terminator sequencing reactions to generate partial cDNA sequences (expressed sequence tags or "ESTs"). The resulting ESTs are analyzed using an Applied Biosystems ABI 3700 sequence analyser.

EXAMPLE 2

Microarray-Based Expression Profiling and Identification of CAD1L Genes from Perennial Ryegrass (*Lolium perenne*)

The function of a gene may be inferred by its co-expression with other genes involved in the same cellular processes. The use of cDNA microarrays allows the expression of thousands of genes to be monitored in one experiment. In this technology a microscope slide is spotted with DNA, each spot containing copies of one gene sequence. The spotted DNA is immobilised on the slide and interrogated with labelled cDNA in solution. The cDNA is prepared from RNA extracted from a tissue of interest and fluorescence-labelled. The amount of fluorescence remaining on the spot after hybridisation with the probe and washing is a measure of the mRNA level of that gene in the tissue of interest. Thousands of these measurements are made from one slide.

The DNA spotted on the perennial ryegrass cDNA slide is derived from EST sequences. Each spot contains an EST that is unique or representative of a unique cluster of ESTs. The putative function of the gene spotted has been inferred by homology searching of the EST sequence against public DNA and protein databases. The results of theses searches demonstrated that around 40% of the genes tagged cannot be assigned a function based on a homology search. However, comparisons of the expression profiles of these unknown genes with those of known genes allows an inference of their function to be made.

In the first experiment mRNA was isolated from the following tissues:

4 day old light grown perennial ryegrass seedlings,
5 day old light grown perennial ryegrass seedling leaves,
7 day old light grown perennial ryegrass seedling leaves,
10 day old light grown perennial ryegrass seedling leaves,
5 day old dark adapted perennial ryegrass seedling leaves,
7 day old dark adapted perennial ryegrass seedling leaves,
10 day old dark adapted perennial ryegrass seedling leaves,
5 day old light grown perennial ryegrass seedling roots,
7 day old light grown perennial ryegrass seedling roots,
10 day old light grown perennial ryegrass seedling roots,
5 day old dark adapted perennial ryegrass seedling roots,
7 day old dark adapted perennial ryegrass seedling roots,
10 day old dark adapted perennial ryegrass seedling roots.

Fluorescence-labelled cDNA was prepared from each RNA preparation. cDNA prepared from 4 day old seedling was used as a common reference probe and used in all the hybridisations. Each of the other treatments was used as a co-hybridisation probe at least once.

In the second experiment RNA was prepared from
leaf blades from mature plants,
roots from mature plants,
pseudostems from mature plants.

Fluorescence-labelled cDNA was prepared from each RNA preparation. cDNA prepared from pseudostems was used as a common reference probe and used in all the hybridisations. Each of the other treatments was used as a co-hybridisation probe at least once. The protocols for these processes are described below.

1. RNA Isolation and Probe Preparation 1.1 Total RNA Isolation

The quality of RNA influences the efficiency of the labelling processes, hybridisation performance and background level. The CTAB protocol has been modified to extract total plant RNA of high purity and quality. The number of extraction steps with chloroform (step 5) is critical to the purity and yield of the isolated RNA. The quality of the isolated RNA is measured using the ratio of absorbance at 230:280, with high quality RNA having a value of around 0.88-1.0. RNA samples that do not meet the quality requirement can be further purified using an RNeasy mini column (Qiagen, Germany) to give microarray quality RNA. However these factors may not be universally applicable and methods for extraction of microarray quality RNA should be optimised for each organism or tissue.

The CTAB protocol [A simple and efficient method for isolating RNA from pine trees. Plant Molecular Biology Reporter (1993) 11(2): 113-116]:

1. Warm 15 ml extraction buffer plus 300 µl β-mercaptoethanol to 65° C. in a water bath.
2. Homogenise 2-3 g tissues in liquid $N_2$ with cooled mortar and pestle.
3. Transfer ground tissues into a 50 ml tube and immerse in liquid $N_2$ bath.
4. Quickly add warmed extraction buffer and mix completely by inverting tube.
5. Add equal volume of chloroform:IAA and vortex the mixture. Spin the tube for 20 min at 5000 rpm at 4° C. in a bench top centrifuge using a swing out rotor (Sigma, USA).
6. Pipette the supernatant (top layer) into a new 50 ml tube. Step 5 is repeated until the interface is clear.
7. Pipette the supernatant into a new 50 ml tube and add 0.25 volume 10 M LiCl. Mix thoroughly and precipitate at 4° C. overnight.
8. Spin the tube for 30 min at 5000 rpm at 4° C. in a bench top centrifuge using a swing out rotor (Sigma, USA).
9. Discard supernatant and dissolve pellet with 500 µl SSTE buffer. Transfer to 1.5 ml Eppendorf tube.
10. Add equal volume of chloroform:IAA and vortex the mixture. Spin the tube for 10 min at 13,000 rpm.
11. Pipette the supernatant into a new 1.5 ml tube and add 2 volumes 100% ethanol. Mix thoroughly and precipitate at −70° C. for 1 h.
12. Spin the tube for 20 min at 13,000 rpm at 4° C.
13. Wash twice with 80% ethanol for 10 min at 13,000 rpm at 4° C.
14. Discard supernatant and air-dry pellet. Resuspend pellet in RNase free water.

1.2 Precipitation of Total RNA

Total RNA is concentrated as follows:

1. Add 0.1 volume 3M sodium acetate pH 5.2 to the RNA solution.
2. Add 3 volumes ethanol to the mixture.
3. Mix thoroughly by inverting the tube.
4. Precipitate at −70° C. for at least 1 h.
5. Centrifuge at 13000 rpm at 4° C. for 30 minutes.
6. Discard supernatant and add 1 ml 70% ethanol.
7. Centrifuge at 13000 rpm at 4° C. for 10 minutes.
8. Discard supernatant and air dry pellet.
9. Resuspend pellet in RNase free water.

1.3 Probe labelling by direct incorporation

Probes are either generated by directly incorporating fluorescent nucleotides during reverse transcription reaction or by indirect methods. Cy3 and Cy5 (either dUTP or dCTP) are generally used as fluorophores as they are compatible with the excitation and emission wavelength of most slide scanners. These fluorochromes are light-sensitive and measures should be taken to minimise their exposure to light.

1. Prepare a 50× low-C dNTP mixture

| | |
|---|---|
| dATP (100 mM) | 25 µl |
| dGTP (100 mM) | 25 µl |
| dTTP (100 mM) | 25 µl |
| dCTP (100 mM) | 10 µl |
| Water | 15 µl |
| Total volume | 100 µl |

2. Mix total RNA with oligo-d(T) in a 200 µl microfuge tube as follows:

| | |
|---|---|
| Total RNA (20 µg) | 10.9 µl |
| Oligo dT12-18 (Gibco, 0.5 µg/µl) | 1.5 µl |

3. Incubate at 70° C. for 10 minutes in a thermal cycler to disrupt RNA secondary structure. Snap cool on ice.
4. While waiting for denaturation, prepare a master mix of the following:

| | 1 sample | 2.5 samples |
|---|---|---|
| 5X Superscript 1st strand buffer | 6 µl | 15 µl |
| DTT (0.1 M) | 3 µl | 7.5 µl |
| 50X dNTP mix | 0.6 µl | 1.5 µl |
| Rnasin (Promega) | 0.5 µl | 1.25 µl |
| Superscript II RT (200 U/µl) | 1.5 µl | 3.75 µl |
| Total volume | 11.6 µl | 29.0 µl |

5. After cooling, add 11.6 µl of master mix from step 4 into each tube. Then add 6 µl of Cy3-dCTP and Cy5-dCTP into the appropriate tubes. Mix well and spin briefly.
6. Incubate at 42° C. for 2 hours in a thermal cycler.
7. Add 1.5 µl 1M NaOH and incubate at 70° C. for 10 min in a thermal cycler to hydrolyse the RNA.
8. Neutralise the reactions by adding 1.5 µl 1 M HCl.
9. Dry down the reaction volume to 20 µl by heating in a thermal cycler set at 80° C. for 15 minutes.
10. The labelled probes are purified using DyeEx column (Qiagen, Germany) or S-400 column (Amersham BioSciences, UK) according to the manufacturer's instructions.
11. Pool the Cy3 and Cy5 labelled probes and dry down to 10 µl for half slide or 20 µl for full slide microarray by heating in a thermal cycler set at 80° C. for 30 minutes. (Note: Do not dry probe completely)
12. The pooled probes are now ready for hybridisation.

2. Prehybridisation Treatment, Hybridisation and Washing

Hybridisations can be carried out under a cover slip placed in a humid hybridisation chamber or a fluidic station. Hybridisation chambers can be obtained from Corning (# 2551) or TeleChem International (# AHC-1). Fluidic stations can be purchased from Amersham Pharmacia Biotech, Affymetrix or Genomic Solutions.

Hybridisations carried out under a cover slip use 15-45 µl of pooled probe depending on the array size. The potential drawback to this method is that the movement of probes is by diffusion. The fluidic station allows a larger volume of pooled probe (100-200 µl) and agitation during hybridisation.

Hybridisations can occur either at 65° C., or 42° C. if 50% formamide is included. General and species specific blocking elements such as CoT-1 DNA, yeast tRNA or poly-d(A) should be included in the hybridisation.

2.1 Immobilising DNA on Glass Slide
1. Bake CMT-GAPS slides (Corning, USA) for 30 minutes at 80° C. in an oven (This protocol can also be used to immobilise DNA onto polylysine coated slides (Sigma, USA)).
2. UV cross-link DNA to slides with 650×100 Joules in Stratalinker (Stratagene, USA).
3. Immerse slides in 95° C. water for 5 min.
4. Immerse in 95% ethanol for 1 min.
5. Dry slides by centrifugation at 800 rpm for 3 min using a 96-well plate rotor (Qiagen, Germany) in a bench-top centrifuge (Sigma, USA).

2.2 Prehybridisation

In principle, prehybridisation is used to block DNA void spaces on the slide to prevent non-specific binding of probes. Generally, prehybridisation on poly-L-lysine or aminosilane coated slide involves two steps. Firstly, the free amine groups on the slide are blocked using succinic anhydride. A condensation reaction takes place and for every succinic anhydride molecule two peptide bonds are formed with the poly-L-lysine and aminosilane. Secondly, DNA void spaces are blocked using salmon sperm DNA. Non specific hybridisation blocker such as Cot-1 DNA or poly-d(A) are also included.

Prehybridisation however is not necessary when using CMT-GAPS slide.

2.3 Hybridisation
1. The volume required for hybridisation is dependent on the size of array used: 15-20 µl for half a glass slide (25×75 mm) and 30 µl for a full glass slide.
2. Mix the pooled labelled probe with hybridisation solution:

|  | Half slide | Full slide |
| --- | --- | --- |
| Labelled probe | 11.4 µl | 22.8 µl |
| 20X SSC | 2.63 µl | 5.26 µl |
| 10% SDS | 0.45 µl | 0.9 µl |
| Poly-adenine (80 µg/µl) | 0.5 µl | 1 µl |
| Total volume | 15 µl | 30 µl |

3. Denature at 98° C. for 2 min and then incubate at 37° C. for 20 min.
4. Pipette the pooled probes on array.
5. Apply cover slip (22×22 mm for half the slide and 22×40 mm for full slide) with care to avoid introducing air bubbles.
6. Pipette 80 µl of 3×SSC into both reservoirs of the hybridisation cassette (Arrayit, USA).
7. Gently place the microarray onto the hybridisation cassette and seal it by screwing tightly.
8. Hybridise at 65° C. for 16-24 h in a water bath excluding light.

2.4 Slide Washing
1. After at least 16 h of hybridisation, the slides are washed in 50 ml tubes in a rotating oven with:

2X SSC, 0.1% SDS for 15 min at RT with shaking
1X SSC for 15 min at 42° C. with shaking
0.1X SSC for 15 min at 68° C. with shaking 2. Dry slides by centrifugation at 800 rpm for 3 min using a 96-well plate rotor (Qiagen, Germany) in a bench-top centrifuge (Sigma, USA).
3. The slides are now ready for scanning.

3. Image Analysis

The slides from each experiment were scanned using a ScanArray 3000 confocal laser scanner. Each scan produced 2 tiff image files, one for the reference probe sample and one for the experimental sample. The intensity information from each pair of images was extracted using Biodiscovery Imagene v5 software, using the default settings. This produces text files describing the intensity of each spot, and various background and quality control measurements. These files were imported into the Biodiscovery GeneSight v 3.2.21 software. In this software duplicate experiments with respect to treatments, were combined and the data normalised. The normalisation procedure used was the default settings for replicated log ratio experiments. This comprises:

Background subtraction using local background,
Substitution of negative values with a value of 20
Take the ratio of the corrected experimental signal to that of the reference sample
Take the log of the ratio to the base 2
Normalise values by the subtraction of the mean log ratio for the treatment or reference being analysed
Combine the replicated values into one value using the data derived from the median signal values, keeping all replicated values.

The log ratios from each experiment are then plotted using the time series tool in the Genesight software. This allows the changes in the expression in the experimental sample relative to the reference sample to be visualised over the time of the experiment. The median signal values are also plotted over time, for both the reference sample and the experimental sample, which allows visual confirmation of the data seen in the log ratio plot.

Once these plots have been produced the expression profile of individual genes can be examined by selecting the gene in the software. This produces a line in each graph. The genes showing the most similar pattern of expression ratios to the selected gene can be chosen by specifying a Euclidian distance within which the software will look for matching genes.

In these experiments the following known lignification genes were used as template genes:

LpCAD1 (gi19849247) represented by spot NcwCADH_LOLPR8639

In each experiment the ratios from each of the time points in the series are plotted from left to right as follows 5 day old dark adapted perennial ryegrass seedling roots,
7 day old dark adapted perennial ryegrass seedling roots,
10 day old dark adapted perennial ryegrass seedling roots
5 day old light grown perennial ryegrass seedling roots,
7 day old light grown perennial ryegrass seedling roots,
10 day old light grown perennial ryegrass seedling roots,
5 day old dark adapted perennial ryegrass seedling leaves,
7 day old dark adapted perennial ryegrass seedling leaves,
10 day old dark adapted perennial ryegrass seedling leaves
5 day old light grown perennial ryegrass seedling leaves,
7 day old light grown perennial ryegrass seedling leaves,
10 day old light grown perennial ryegrass seedling leaves, (all versus 4 day old light grown whole seedling)
mature roots
mature leaves
imbibed seed, (all versus mature pseudostem)

The identities of the spots with similar ratios to LpCAD1 are given in Table 2.

TABLE 2

Identities of the spots with similar ratios to LpCAD1

| Spot ID | Spot annotation |
|---|---|
| CccFTSH__RICPR19091 | FtsH protease, putative |
| BcwPME1__CITSI20419 | pectin methyl esterase like protein |
| DdrGTH1__MAIZE10832 | rice-*Oryza sativa* mRNA for glutathione S-transferase, RGST I |
| XnsDDXY__HUMAN14896 | arab-*Arabidopsis thaliana* mRNA for ceo protein |
| DdtGTH2__WHEAT21022 | rice-*Oryza sativa* mRNA for glutathione S-transferase, RGST I |
| U-20rg2DsD024127 | arab-A. thaliana RPM1 gene.\|disease resistance gene\| |
| DdtGTX2__TOBAC11032 | arab-*Arabidopsis thaliana* mRNA glutathione S-transferase |
| EtcIDH1__YEAST13724 | arab-*Arabidopsis thaliana* NAD+ dependent isocitrate dehydrogenase subunit 1 (IDH1) |
| XnsPER__DROWI-16682 | putative RING zinc finger protein |
| MaaATTY__RAT--12398 | putative protein |
| McaDHSO__RAT--19532 | sorbitol dehydrogenase-like protein/; supported by full-length cDNA: Ceres: 13875. |
| U-11rg1NsE116764 | unknown protein |
| QpdORYA__ORYSA14453 | rice-Rice mRNA for oryzain Alpha |
| PtfIF43__NICPL22500 | eukaryotic translation initiation factor 4A (eIF-4A), putative |
| PtsSYR__SYNY3-16812 | arginyl tRNA synthetase |
| NcwCADH__LOLPR8639 | arab-*Arabidopsis thaliana* putative cinnamyl Alcohol dehydrogenase 2 |
| NcwZRP4__MAIZE11604 | O methyltransferase like protein |
| XnsCDPK__DAUCA21088 | calcium dependent protein kinase |
| SmeP2C2__SCHPO13117 | protein phosphatase 2C like |
| TxxRUXG__ARATH10451 | putative small nuclear ribonucleoprotein polypeptide G |
| XnsMYC__HUMAN-22170 | putative protein |
| XnsTP2M__DICDI19579 | No known database match |
| XnsYM68__CAEEL8677 | No known database match |
| XnsHBP__HORVU-21389 | No known database match |
| XnsE1BL__ADEM110461 | No known database match |
| XnsYQCF__BACSU19429 | No known database match |
| U-11rg2FsF117348 | No known database match |
| XnsIF3__MYCFE-17137 | No known database match |
| XnsRBL__EPASP-16624 | No known database match |
| XnsFLGA__AGRTU16541 | No known database match |
| XnsRL2A__TRYBB14244 | No known database match |
| XnsYEO1__YEAST13387 | No known database match |
| U-07rg1BsC012392 | No known database match |
| XnsYC45__ODOSI22879 | No known database match |
| XnsSYTC__ARATH15106 | No known database match |
| XnsHRL2__LACMU16714 | arab-*Arabidopsis thaliana* 2-on-2 hemoglobin (GLB3) mRNA, complete cds.\|\|2-on-2 hemoglobin |
| XnsMFD__BACSU-21643 | arab-*Arabidopsis thaliana* AT5g40660/MNF13__180 mRNA, complete cds.\|unknown protein\|AT5g40660/MNF13__180 |
| XnsTRA1__CAEEL17332 | putative protein |
| XnsNPA2__HUMAN19630 | putative protein |
| XnsSRY__MOUSE-23681 | putative protein |
| ZhyYN45__YEAST16820 | putative protein |
| XnsPER__DROPS-8480 | putative protein |
| U-07rg1UsB012908 | No known database match |

The sequence identifiers associated with the spot IDs and the number of ESTs represented by the cluster are shown in Table 3.

TABLE 3

Identification of representative ESTs and size of EST cluster

| Spot ID | Representative EST | ESTs in cluster |
|---|---|---|
| CccFTSH__RICPR19091 | 13rg2HsF03 | 1 |
| BcwPME1__CITSI20419 | 15rg1IsE04 | 2 |
| DdrGTH1__MAIZE10832 | 03rg1BsC11 | 2 |
| XnsDDXY__HUMAN14896 | 10rg1FsA11 | 1 |
| DdtGTH2__WHEAT21022 | 17rg1FsE05 | 1 |
| U-20rg2DsD024127 | 20rg2DsD01 | 1 |
| DdtGTX2__TOBAC11032 | 04rg1EsH08 | 7 |
| EtcIDH1__YEAST13724 | 08rg1EsF12 | 1 |
| XnsPER__DROWI-16682 | 11rg1KsD06 | 7 |
| MaaATTY__RAT--12398 | 07rg1BsD10 | 2 |
| McaDHSO__RAT--19532 | 14rg1KsH02 | 1 |
| U-11rg1NsE116764 | 11rg1NsE11 | 16 |
| QpdORYA__ORYSA14453 | 08rg1XsH02 | 28 |
| PtfIF43__NICPL22500 | 19rg2PsG09 | 1 |
| PtsSYR__SYNY3-16812 | 11rg1PsA11 | 3 |
| NcwCADH__LOLPR8639 | 01rg1JsC01 | 1 |
| NcwZRP4__MAIZE11604 | 06rg1PsG08 | 1 |
| XnsCDPK__DAUCA21088 | 17rg1HsA09 | 1 |
| SmeP2C2__SCHPO13117 | 07rg1YsG09 | 9 |
| TxxRUXG__ARATH10451 | 01rg1OsC05 | 6 |
| XnsMYC__HUMAN-22170 | 19rg1UsD06 | 10 |
| XnsTP2M__DICDI19579 | 14rg1MsF01 | 1 |
| XnsYM68__CAEEL8677 | 01rg1KsA11 | 4 |
| XnsHBP__HORVU-21389 | 17rg1PsH08 | 1 |

TABLE 3-continued

Identification of representative ESTs and size of EST cluster

| Spot ID | Representative EST | ESTs in cluster |
|---|---|---|
| XnsE1BL__ADEM110461 | 01rg1OsE05 | 1 |
| XnsYQCF__BACSU19429 | 14rg1GsH12 | 1 |
| U-11rg2FsF117348 | 11rg2FsF10 | 1 |
| XnsIF3__MYCFE-17137 | 11rg1YsE05 | 4 |
| XnsRBL__EPASP-16624 | 11rg1IsG04 | 1 |
| XnsFLGA__AGRTU16541 | 11rg1GsE08 | 1 |
| XnsRL2A__TRYBB14244 | 08rg1TsF06 | 1 |
| XnsYEO1__YEAST13387 | 07rg2JsB02 | 1 |
| U-07rg1BsC012392 | 07rg1BsC02 | 1 |
| XnsYC45__ODOSI22879 | 22rg1BsE12 | 1 |
| XnsSYTC__ARATH15106 | 10rg1PsF07 | 1 |
| XnsHRL2__LACMU16714 | 11rg1LsD06 | 1 |
| XnsMFD__BACSU-21643 | 17rg1VsH11 | 1 |
| XnsTRA1__CAEEL17332 | 11rg2FsC02 | 1 |
| XnsNPA2__HUMAN19630 | 14rg1OsC04 | 2 |
| XnsSRY__MOUSE-23681 | 28rg1EsC06 | 1 |
| ZhyYN45__YEAST16820 | 11rg1PsC08 | 1 |
| XnsPER__DROPS-8480 | 01rg1DsD03 | 1 |
| U-07rg1UsB012908 | 07rg1UsB03 | 1 |

The clusters with no known database match represented by ESTs 14rg1MsF01, 01rg1KsA11, 17rg1PsH08, 01rg10sE05, 14rg1GsH12, 11rg2FsF10, 11rg1YsE05, 11rg1IsG04, 11rg1GsE08, 08rg1TsF06, 07rg2JsB02, 07rg1BsC02, 22rg1BsE12, 10rg1PsF07 allowed the identification of LpCAD1L and LpCAD1L-like genes.

4. Identification of CAD1L Genes

Candidate ESTs identified by microarray expression profiling were further analysed by visual inspection of their sequencing trace files and CAD1L genes were selected based on sequence quality assessment. Table 4 summarises the selected cDNA clones (indicating EST code on microarray) coding for CAD1L enzymes identified by microarray expression profiling and provides the sequence name for the perennial ryegrass CAD1L cDNA sequences.

TABLE 4

Identification of CAD1L genes from perennial ryegrass using LpCAD1 as template gene

| EST code on microarray | LpCAD1L sequence name |
|---|---|
| 01rg1OsE05 | LpCAD1La |
| 11rg1IsG04 | LpCAD1Lb |
| 11rg1YsE05 | LpCAD1Lc |
| 11rg2FsF10 | LpCAD1Ld |
| 14rg1GsH12 | LpCAD1Le |
| 14rg1MsF01 | LpCAD1Lf |

EXAMPLE 4

Development of a Binary Transformation Vector Containing Chimeric Genes with the cDNA Sequences from Perennial Ryegrass CAD1La, CAD1Lb, CAD1Lc, CAD1Ld, CAD1Le and CAD1Lf To alter the expression of the perennial ryegrass CAD1La, CAD1Lb, CAD1Lc, CAD1Ld, CAD1Le and CAD1Lf, sense and antisense binary transformation vectors are produced.

The pPZP221 binary transformation vector (Hajdukiewicz et al., 1994) was modified to contain the $35S^2$ cassette from pKYLX71:$35S^2$ (Schardl et al., 1987) as follows: pKYLX71:$35S^2$ was cut with CiaI. The 5' overhang was filled in using Klenow and the blunt end was A-tailed with Taq polymerase. After cutting with EcoRI, the 2 kb fragment with an EcoRI-compatible and a 3'-A tail was gel-purified. pPZP221 was cut with HindIII and the resulting 5' overhang filled in and T-tailed with Taq polymerase. The remainder of the original pPZP221 multi-cloning site was removed by digestion with EcoRI, and the expression cassette cloned into the EcoRI site and the 3' T overhang restoring the HindIII site. This binary vector contains between the left and right border the plant selectable marker gene aacC1 under the control of the 35S promoter and 35S terminator and the pKYLX71:$35S^2$-derived expression cassette with a CaMV 35S promoter with a duplicated enhancer region and an rbcS terminator.

A GATEWAY® cloning cassette (Invitrogen) was introduced into the multicloning site of the pPZP221:$35S^2$ vector obtained as described following the manufacturer's protocol.

The LpCAD1La, LpCAD1Lb, LpCAD1Lc, LpCAD1Ld, LPCAD1Le and LpCAD1Lf cDNA fragments are generated by high fidelity PCR with a proofreading DNA polymerase using the original pGEM-T Easy plasmid cDNAs as a template. The primers used (Table 6) contained attb sequences for use with recombinases utilising the GATEWAY® system (Invitrogen). The resulting PCR fragments are used in a recombination reaction with pDONR® vector (Invitrogen) to generate entry vectors. In a further recombination reaction, the cDNAs are transferred from the entry vectors to the GATEWAY®-enabled pPZP221:$35S^2$ vector.

The orientation of the constructs (sense or antisense) is checked by restriction enzyme digest and sequencing which also confirms the correctness of the sequence. Transformation vectors containing chimeric genes using cDNAs representing perennial ryegrass CAD1La, CAD1Lb, CAD1Lc CAD1Ld, CAD1Le and CAD1Lf in sense and antisense orientation under the control of the CaMV $35S^2$ promoter are generated (FIGS. 4, 6, 8, 10, 12 and 14).

TABLE 6

List of primers used to PCR-amplify the cDNAs of LpCAD1La, LpCAD1Lb, LpCAD1Lc, LpCAD1Ld, LpCAD1Le and LpCAD1Lf

| gene name | orientation | primer | primer sequence (5'->3') |
|---|---|---|---|
| LpCAD1La | sense | forward | GGGGACAAGTTTGTACAAAA AAGCAGGCTGAGCATGGATG ATTTTTAAGTCTG |
| | | reverse | GGGGACCACTTTGTACAAGA AAGCTGGGTCCCACACCACA AAAACTGTTCG |
| | antisense | forward | GGGGACCACTTTGTACAAGA AAGCTGGGTGAGCATGGATG ATTTTTAAGTCTG |
| | | reverse | GGGGACAAGTTTGTACAAAA AAGCAGGCTCCCACACCACA AAAACTGTTCG |
| LpCAD1Lb | sense | forward | GGGGACAAGTTTGTACAAAA AAGCAGGCTATTCAAGGCCA TCTATTACAGTAGC |
| | | reverse | GGGGACCACTTTGTACAAGA AAGCTGGGTAAGAGAACACA TAGAAGCTTTGC |
| | antisense | forward | GGGGACCACTTTGTACAAGA AAGCTGGGTATTCAAGGCCA TCTATTACAGTAGC |
| | | reverse | GGGGACAAGTTTGTACAAAA AAGCAGGCTAAGAGAACACA TAGAAGCTTTGC |

TABLE 6-continued

List of primers used to PCR-amplify the
cDNAs of LpCAD1La, LpCAD1Lb, LpCAD1Lc,
LpCAD1Ld, LpCAD1Le and LpCAD1Lf

| gene name | orientation | primer | primer sequence (5'->3') |
|---|---|---|---|
| LpCAD1Lc | sense | forward | GGGGACAAGTTTGTACAAAA AAGCAGGCTGGTGTCGGAGG ATCTGATTTCC |
| | | reverse | GGGGACCACTTTGTACAAGA AAGCTGGGTCAGCATTGAAT GGAACAGAC |
| | antisense | forward | GGGGACCACTTTGTACAAGA AAGCTGGGTGGTGTCGGAGG ATCTGATTTCC |
| | | reverse | GGGGACAAGTTTGTACAAAA AAGCAGGCTCAGCATTGAAT GGAACAGAC |
| LpCAD1Ld | sense | forward | GGGGACAAGTTTGTACAAAA AAGCAGGCTTATCCTTGCTT CAGCTTTAGC |
| | | reverse | GGGGACCACTTTGTACAAGA AAGCTGGGTCAAGAAAAGGA AATAAACCCCTAAAAC |
| | antisense | forward | GGGGACCACTTTGTACAAGA AAGCTGGGTTATCCTTGCTT CAGCTTTAGC |
| | | reverse | GGGGACAAGTTTGTACAAAA AAGCAGGCTCAAGAAAAGGA AATAAACCCCTAAAAC |
| LpCAD1Le | sense | forward | GGGGACAAGTTTGTACAAAA AAGCAGGCTGAGCATTCATC TGGTAGAAACC |
| | | reverse | GGGGACCACTTTGTACAAGA AAGCTGGGTAAGTAGTTTTG TTGCTGGTGCAAAGC |
| | antisense | forward | GGGGACCACTTTGTACAAGA AAGCTGGGTGAGCATTCATC TGGTAGAAACC |
| | | reverse | GGGGACAAGTTTGTACAAAA AAGCAGGCTAAGTAGTTTTG TTGCTGGTGCAAAGC |
| LpCAD1Lf | sense | forward | GGGGACAAGTTTGTACAAAA AAGCAGGCTGAGCATTTAAC TTATTTATCAG |
| | | reverse | GGGGACCACTTTGTACAAGA AAGCTGGGTGGTACTTAAGA TTATTGTCTAACTG |
| | antisense | forward | GGGGACCACTTTGTACAAGA AAGCTGGGTGAGCATTTAAC TTATTTATCAG |
| | | reverse | GGGGACAAGTTTGTACAAAA AAGCAGGCTGGTACTTAAGA TTATTGTCTAACTG |

EXAMPLE 5

Production and Analysis of Transgenic *Arabidopsis* Plants Carrying the Chimeric Perennial Ryegrass Gene CAD1La, CAD1Lb, CAD1Lc, CAD1Ld, CAD1Le and CAD1Lf A set of transgenic *Arabidopsis* plants carrying the chimeric perennial ryegrass gene CAD1La, CAD1Lb, CAD1Lc, CAD1Ld, CAD1Le and CAD1Lf are produced.

A set of pPZP221-based transformation vectors with LpCAD1La, LpCAD1Lb, LpCAD1Lc, LpCAD1Ld, LpCAD1Le and LpCAD1Lf cDNAs in sense and antisense orientation under the control of the CaMV 35S promoter with duplicated enhancer region ($35S^2$) are generated as detailed in Example 6.

*Agrobacterium*-mediated gene transfer experiments are performed using these transformation vectors.

The production of transgenic *Arabidopsis* plants carrying the perennial ryegrass CAD1La, CAD1Lb, CAD1Lc, CAD1Ld, CAD1Le and CAD1Lf cDNA under the control of the CaMV 35S promoter with duplicated enhancer region ($35S^2$) is described here in detail.

Preparation of *Arabidopsis* Plants

Seedling punnets are filled with Debco™ seed raising mixture (Debco Pty. Ltd.) to form a mound. The mound is covered with two layers of anti-bird netting secured with rubber bands on each side. The soil is saturated with water and enough seeds (*Arabidopsis thaliana* ecotype Columbia, Lehle Seeds #WT-02) sown to obtain approximately 15 plants per punnet. The seeds are then vernalised by placing the punnets at 4° C. After 48 hours the punnets are transferred to a growth room at 22° C. under fluorescent light (constant illumination, 55 $\mu molm^{-2}s^{-1}$) and fed with Miracle-Gro™ (Scotts Australia Pty. Ltd.) once a week. Primary bolts are removed as soon as they appear. After 4-6 days the secondary bolts are approximately 6 cm tall, and the plants are ready for vacuum infiltration.

Preparation of *Agrobacterium*

*Agrobacterium tumefaciens* strain AGL-1 is streaked on LB medium containing 50 µg/ml rifampicin and 50 µg/ml kanamycin and grown at 27° C. for 48 hours. A single colony is used to inoculate 5 ml of LB medium containing 50 µg/ml rifampicin and 50 µg/ml kanamycin and grown over night at 27° C. and 250 rpm on an orbital shaker. The overnight culture is used as an inoculum for 500 ml of LB medium containing 50 µg/ml kanamycin only. Incubation is over night at 27° C. and 250 rpm on an orbital shaker in a 2 l Erlenmeyer flask.

The overnight cultures are centrifuged for 15 min at 5500×g and the supernatant discarded. The cells are resuspended in 1 l of infiltration medium [5% (w/v) sucrose, 0.03% (v/v) Silwet-L77 (Vac-In-Stuff, Lehle Seeds #VIS-01)] and immediately used for infiltration.

Vacuum Infiltration

The *Agrobacterium* suspension is poured into a container (Décor Tellfresh storer, #024) and the container placed inside the vacuum desiccator (Bel Art, #42020-0000). A punnet with *Arabidopsis* plants is inverted and dipped into the *Agrobacterium* suspension and a gentle vacuum (250 mm Hg) is applied for 2 min. After infiltration, the plants are returned to the growth room where they are kept away from direct light overnight. The next day the plants are returned to full direct light and allowed to grow until the siliques are fully developed. The plants are then allowed to dry out, the seed collected from the siliques and either stored at room temperature in a dry container or used for selection of transformants.

Selection of Transformants

Prior to plating the seeds are sterilised as follows. Sufficient seeds for one 150 mm petri dish (approximately 40 mg or 2000 seeds) are placed in a 1.5 ml microfuge tube. 500 µl 70% ethanol are added for 2 min and replaced by 500 µl sterilisation solution ($H_2O$:4% chlorine:5% SDS, 15:8:1). After vigorous shaking, the tube is left for 10 min after which time the sterilisation solution is replaced with 500 µl sterile water. The tube is shaken and spun for 5 sec to sediment the seeds. The washing step is repeated 3 times and the seeds are left covered with approximately 200 µl sterile water.

The seeds are then evenly spread on 150 mm petri dishes containing germination medium (4.61 g Murashige & Skoog salts, 10 g sucrose, 1 ml 1 M KOH, 2 g Phytagel, 0.5 g MES and 1 ml 1000× Gamborg's B-5 vitamins per litre) supplemented with 250 μg/ml timetin and 75 μg/ml gentamycin. After vernalisation for 48 hours at 4° C. the plants are grown under continuous fluorescent light (55 μmol m-2s-1) at 22° C. to the 6-8 leaf stage, transferred to soil and grown to seeding stage using the Arasystem (Betatech, Belgium).

Preparation of Genomic DNA 3-4 leaves of *Arabidopsis* plants regenerated on selective medium are harvested and freeze-dried. The tissue is homogenised on a Retsch MM300 mixer mill, then centrifuged for 10 min at 1700×g to collect cell debris. Genomic DNA is isolated from the supernatant using Wizard Magnetic 96 DNA Plant System kits (Promega) on a Biomek FX (Beckman Coulter). 5 μl of the sample (50 μl) are then analysed on an agarose gel to check the yield and the quality of the genomic DNA.

Analysis of DNA using Real-Time PCR

Genomic DNA is analysed for the presence of the transgene by real-time PCR using SYBR Green chemistry. PCR primer pairs (Table 7) are designed using Primer Express 1.5. The forward primer is located within the $35S^2$ promoter region and the reverse primer within the transgene to amplify products of approximately 150 bp as recommended. The positioning of the forward primer within the $35S^2$ promoter region guarantees that homologous genes in *Arabidopsis* are not detected.

5 μl of each genomic DNA sample are run in a 50 μl PCR reaction including SYBR Green on an ABI7700 (Applied Biosystems) together with samples containing DNA isolated from wild type *Arabidopsis* plants (negative control), samples containing buffer instead of DNA (buffer control) and samples containing the plasmid used for transformation (positive plasmid control).

Figure 15:
FIG. 15 shows *Agrobacterium*-mediated transformation and selection of *Arabidopsis*.

Plants are obtained after transformation with all chimeric constructs and selection on medium containing gentamycin. The transformation and selection process is shown in FIG. 15.

TABLE 7

List of primers used for real time PCR analysis of Arabidopsis plants transformed with LpCAD1La, LpCAD1Lb, LpCAD1Lc, LpCAD1Ld, LpCAD1Le and LpCAD1Lf

| gene name | orientation | primer | primer sequence (5'->3') |
|---|---|---|---|
| LpCAD1La | sense | forward | GGAGAGGACACGCTGAAATCA |
| | | reverse | CACCACAAAAACTGTTCCGCTAGA |
| | antisense | forward | CAATCCCACTATCCTTCGCAA |
| | | reverse | AGCCCTGTGACTGACAGCG |
| LpCAD1Lb | sense | forward | TTCATTTGGAGAGGACACGCT |
| | | reverse | TTCTTTCCCTTCCAATCTCCC |
| | antisense | forward | AGGAAGTTCATTTCATTTGGAGAGG |
| | | reverse | TGAGCTATCATCATCTGCCTGC |
| LpCAD1Lc | sense | forward | ATGACGCACAATCCCACTATCC |
| | | reverse | AACACAAGAGGGAGAAGAGGGG |

TABLE 7-continued

List of primers used for real time PCR analysis of Arabidopsis plants transformed with LpCAD1La, LpCAD1Lb, LpCAD1Lc, LpCAD1Ld, LpCAD1Le and LpCAD1Lf

| gene name | orientation | primer | primer sequence (5'->3') |
|---|---|---|---|
| | antisense | forward | CTGACGTAAGGGATGACGCA |
| | | reverse | TGGTTTGGATTTGTCTGTTCCA |
| LpCAD1Ld | sense | forward | CGTAAGGGATGACGCACAATC |
| | | reverse | GAATCACAGCTGGAAGCTAAAGC |
| | antisense | forward | TTCATTTGGAGAGGACACGCT |
| | | reverse | CGGTGTTTGTTTTGCAGGTG |
| LpCAD1Le | sense | forward | CCACTATCCTTCGCAAGACCC |
| | | reverse | CGCGAGCATTCTTTTAGCATT |
| | antisense | forward | TGACGCACAATCCCACTATCC |
| | | reverse | TGTTTTCAGCAACCAAGCTTTG |
| LpCAD1Lf | sense | forward | AGGAAGTTCATTTCATTTGGAGAGG |
| | | reverse | AGTATGTGTGTGTTGAGCACTTCG |
| | antisense | forward | TCATTTGGAGAGGACACGCTG |
| | | reverse | ATCCACGAAGTAAATTCAAACCCT |

Finally, it is to be understood that various alterations, modifications and/or additions may be made without departing from the spirit of the present invention as outlined herein.

Documents cited in this specification are for reference purposes only and their inclusion is not acknowledgment that they form part of the common general knowledge in the relevant art.

REFERENCES

Frohman, M. A., Dush, M. K., Martin, G. R. (1988) Rapid production of full-length cDNAs from rare transcripts: amplification using a single gene-specific oligonucleotide primer. *Proc. Natl. Acad. Sci.* USA 85, 8998.

Hajdukiewicz P, Svab Z, Maliga P. (1994) The small, versatile pPZP family of *Agrobacterium* binary vectors for plant transformation. Plant Mol Biol. 25, 989-94.

Loh, E. Y., Ellioft, J. F., Cwirla, S., Lanier, L. L., Davis, M. M. (1989). Polymerase chain reaction with single-sided specificity: Analysis of T-cell receptor delta chain. *Science* 243, 217-220.

Ohara, O., Dorit, R. L., Gilbert, W. (1989). One-sided polymerase chain reaction: The amplification of cDNA. *Proc. Natl. Acad Sci* USA 86, 5673-5677

Sambrook, J., Fritsch, E. F., Maniatis, T. (1989). Molecular Cloning. A Laboratory Manual. Cold Spring Harbour Laboratory Press Schardl, C. L., Byrd, A. D., Benzion, G., Altschuler, M. A., Hildebrand, D. F., Hunt, A. G. (1987) Design and construction of a versatile system for the expression of foreign genes in plants. Gene 61, 1-11

The invention claimed is:

1. A substantially purified or isolated nucleic acid having a length of at least 30 nucleotides, wherein the entire nucleic acid is at least approximately 95% identical to a segment of equal length in SEQ ID No: 2, or at least approximately 95% identical to the DNA complement of a segment of equal length in SEQ ID No: 2, or the RNA equivalents thereof.

2. The nucleic acid of claim 1, comprising a nucleotide sequence selected from the group consisting of (a) SEQ ID No: 2, and (b) the complement of Seq ID No. 2.

3. A construct comprising one or more nucleic acids according to claim 2.

4. The construct according to claim 3 wherein the one or more nucleic acids are operably linked to one or more regulatory elements, such that the one or more nucleic acids are each expressed.

5. The construct according to claim 4, wherein the one or more regulatory elements include an operably linked promoter and an operably linked terminator.

6. A plant cell, plant, plant seed or other plant part, including a construct according to claim 3.

7. A plant, plant seed or other plant part, derived from a plant cell or plant according to claim 6, wherein said derived plant, plant seed or other plant part comprises the construct.

8. A method of modifying one or more of lignification, defence response, or cell walls in a plant, said method including introducing into said plant an effective amount of the nucleic acid according to claim 2.

9. A preparation for transforming a plant comprising the nucleic acid according to claim 2.

10. The nucleic acid of claim 1, wherein the nucleic acid has a length of at least 45 nucleotides.

11. The nucleic acid of claim 1, wherein the nucleic acid has a length of at least 60 nucleotides.

12. The nucleic acid of claim 1, wherein the nucleic acid is at least 95% identical to the entirety of SEQ ID No: 2 or at least 95% identical to the complement of the entirety of SEQ ID No: 2.

13. The nucleic acid of claim 12, wherein the nucleic acid differs from SEQ ID No: 2 as a consequence of one or more nucleic acid changes and wherein all of the changes result in conservative amino acid substitutions in the corresponding amino acid sequence.

14. The nucleic acid of claim 12, wherein the nucleic acid differs from SEQ ID No: 2 at a single nucleotide.

15. The nucleic acid of claim 1 comprising the nucleotide sequence of SEQ ID No: 2.

16. The nucleic acid of claim 1, wherein the entire nucleic acid is 100% identical to a segment of equal length in SEQ ID No: 2 or 100% identical to DNA complement of a segment of equal length in SEQ ID No: 2, or the RNA equivalents thereof.

* * * * *